US012778567B2

(12) United States Patent
Qiang et al.

(10) Patent No.: US 12,778,567 B2
(45) Date of Patent: Nov. 3, 2026

(54) DELIVERY ACTUATOR AND DELIVERY APPARATUS

(71) Applicant: BEIJING MED-ZENITH MEDICAL SCIENTIFIC CORPORATION LIMITED, Beijing (CN)

(72) Inventors: Yanxin Qiang, Beijing (CN); Zhiwei Ma, Beijing (CN); Qingliang Zhou, Beijing (CN)

(73) Assignee: BEIJING MED-ZENITH MEDICAL SCIENTIFIC CORPORATION LIMITED, Beijing (CN)

( * ) Notice: Subject to any disclaimer, the term of this patent is extended or adjusted under 35 U.S.C. 154(b) by 51 days.

(21) Appl. No.: 18/994,465

(22) PCT Filed: Jul. 13, 2023

(86) PCT No.: PCT/CN2023/107223

§ 371 (c)(1),
(2) Date: Jan. 14, 2025

(87) PCT Pub. No.: WO2024/012525

PCT Pub. Date: Jan. 18, 2024

(65) Prior Publication Data

US 2026/0033819 A1 Feb. 5, 2026

(30) Foreign Application Priority Data

Jul. 14, 2022 (CN) ........................ 202210833993.5

(51) Int. Cl.
*A61B 17/00* (2006.01)
*A61B 17/122* (2006.01)
(Continued)

(52) U.S. Cl.
CPC ........ *A61B 17/0057* (2013.01); *A61B 17/122* (2013.01); *A61B 17/1285* (2013.01);
(Continued)

(58) Field of Classification Search
CPC .............. A61B 17/0057; A61B 17/122; A61B 17/1285; A61B 90/03; A61B 2017/00367;
(Continued)

(56) References Cited

U.S. PATENT DOCUMENTS 5,891,162 A * 4/1999 Sugarbaker ............ A61B 17/29
606/151
6,364,879 B1 * 4/2002 Chen .................. A61B 17/2804
606/49
(Continued)

FOREIGN PATENT DOCUMENTS

CN 107157542 A 9/2017
CN 107433608 A 12/2017
(Continued)

OTHER PUBLICATIONS

1 The extended European search report of counterpart EP application 23839015.7 was issued on Oct. 14, 2025.
(Continued)

*Primary Examiner* — Andrew Restaino
(74) *Attorney, Agent, or Firm* — Scully, Scott, Murphy & Presser, P.C.

(57) ABSTRACT

A delivery actuator and a delivery apparatus are provided. The delivery actuator includes a swing seat, a first tong arm, a second tong arm, and a connecting rod mechanism. The swing seat is rotatably connected to a base. In the connecting rod mechanism, a first connecting rod and a second connecting rod are hinged to each other, and the first connecting rod and the second connecting rod form an X-shaped scissor structure. A hinge shaft of the first connecting rod and the second connecting rod is hinged to the swing seat. First ends of the first connecting rod and the second connecting rod are respectively hinged to the first tong arm and the second tong arm, and second ends of the first connecting rod and the
(Continued)

second connecting rod are respectively hinged to first ends of a third connecting rod and a fourth connecting rod.

12 Claims, 18 Drawing Sheets

(51) Int. Cl.
*A61B 17/128* (2006.01)
*A61B 90/00* (2016.01)

(52) U.S. Cl.
CPC .... *A61B 90/03* (2016.02); *A61B 2017/00367* (2013.01); *A61B 2017/00477* (2013.01); *A61B 2017/00584* (2013.01); *A61B 2017/00623* (2013.01); *A61B 2017/00632* (2013.01); *A61B 2090/034* (2016.02)

(58) Field of Classification Search
CPC ........... A61B 2017/00477; A61B 2017/00584; A61B 2017/00623; A61B 2017/00632; A61B 2090/034; A61B 2017/00243; A61B 2017/2927; A61B 2017/2937; A61B 2017/2939; A61B 2017/2944; A61B 17/1227; A61B 17/128
See application file for complete search history.

(56) References Cited

U.S. PATENT DOCUMENTS

| | | | | | |
|---|---|---|---|---|---|
| 6,582,451 | B1* | 6/2003 | Marucci | A61B 17/29 | 606/207 |
| 2005/0090817 | A1* | 4/2005 | Phan | A61B 18/1445 | 606/41 |
| 2005/0165429 | A1* | 7/2005 | Douglas | A61B 17/122 | 606/157 |
| 2010/0256768 | A1* | 10/2010 | Lim | A61B 17/8858 | 606/86 A |
| 2015/0032125 | A1* | 1/2015 | Jeong | A61B 34/71 | 606/130 |
| 2021/0298900 | A1 | 9/2021 | Zhao | | |
| 2022/0211384 | A1 | 7/2022 | Shi | | |

FOREIGN PATENT DOCUMENTS

| | | | | |
|---|---|---|---|---|
| CN | 107932024 | A | 4/2018 | |
| CN | 209289308 | U | 8/2019 | |
| CN | 111449696 | A | 7/2020 | |
| CN | 210938848 | U | 7/2020 | |
| CN | 211073598 | U | 7/2020 | |
| CN | 211409200 | U | 9/2020 | |
| CN | 112336403 | A | 2/2021 | |
| CN | 113662613 | A | 11/2021 | |
| CN | 113662614 | A | 11/2021 | |
| CN | 113662615 | A | 11/2021 | |
| CN | 113662616 | A | 11/2021 | |
| CN | 218247293 | U | 1/2023 | |
| DE | 4412171 | A1 * | 10/1995 | A61B 17/0218 |
| JP | 2009-11698 | A | 1/2009 | |
| JP | 2010-512852 | A | 4/2010 | |
| JP | 2017-23701 | A | 2/2017 | |
| JP | 2018-340 | A | 1/2018 | |
| WO | 2017167349 | A1 | 10/2017 | |
| WO | 2022127561 | A1 | 6/2022 | |

OTHER PUBLICATIONS

Japanese Notice of Reasons for Refusal dated Dec. 12, 2025 received in Japanese Patent Application No. 2025-501459.
The first office action of counterpart CN application 2022108339935 was issued on Oct. 23, 2023.
The search report of PCT application No. PCT/CN2023/107223 issue on Oct. 20, 2023.

* cited by examiner

DELIVERY ACTUATOR AND DELIVERY APPARATUS

CROSS-REFERENCE TO RELATED APPLICATION

The present disclosure claims priority to Chinese Patent Application No. 202210833993.5, filed to the China National Intellectual Property Administration on Jul. 14, 2022 and entitled “Delivery Actuator and Delivery Apparatus”, the disclosure of which is hereby incorporated by reference in its entirety.

TECHNICAL FIELD

The present disclosure relates to the field of medical instruments, particularly to a delivery actuator and a delivery apparatus.

BACKGROUND

Atrial fibrillation is one of the most common arrhythmias in clinical practice. The consequences of cerebral apoplexy caused by atrial fibrillation are very serious, and the death rate and disability rate can reach 70%. For patients with valvular atrial fibrillation, 57% of atrial thrombi originate from the left auricle. For patients with non-valvular atrial fibrillation, 90% of left atrial thrombi originate from the left auricle. Even if the sinus rhythm is restored, the contraction of the left auricle is suppressed, which may still lead to the formation of thrombi.

At present, there are three main methods for preventing ischemic cerebral apoplexy caused by atrial fibrillation in clinical practice. The first method is to take an anticoagulant drug such as warfarin. However, the use of warfarin has a certain risk of bleeding and requires frequent monitoring, there are many contraindications, and the clinical application is relatively difficult. In addition, warfarin may also cause osteoporosis and soft tissue necrosis. The second method is to directly excise or ligate the auricle during a cardiac surgery. The main defect of this method is that the complete closure rate of the left auricle is relatively low. Previous studies have shown that the highest success rate of completely excising the left auricle is about 80%. The third method is to close the left auricle through an instrument such as an auricle clamp to perform percutaneous intracardiac intervention for left auricle occlusion. However, delivery devices of such products are complex in operation and higher in risk, and the safety and effectiveness need to be verified.

An auricle clamp delivered by an existing auricle clamp delivery apparatus generally includes two parallel clamp arms and is also provided with two spring parts, the two spring parts are located at two ends of the auricle clamp, and the clamping of the two clamp arms can be maintained through the two spring parts. The front end of the auricle clamp delivery apparatus is usually provided with a slightly square outer frame to facilitate the binding of the auricle clamp therein, and the outer frame of the delivery apparatus uses a traction rope to hold the clamp arms of the auricle clamp so as to tighten the traction rope to pull the auricle clamp open, thereby driving the auricle clamp to be delivered to the focus to perform the extracardiac closure operation of the left auricle.

In the above auricle clamp delivery apparatus, how to achieve parallel closing and opening of the two clamp arms of the auricle clamp with a simple and convenient structure is a problem that needs to be solved.

SUMMARY

The present disclosure provides a delivery actuator and a delivery apparatus to solve the above technical problems in the prior art.

The delivery actuator provided by the present disclosure includes a swing seat, a first tong arm, a second tong arm, and a connecting rod mechanism; the swing seat is connected to a base and is rotatably connected to the base; the connecting rod mechanism includes a first connecting rod, a second connecting rod, a third connecting rod, a fourth connecting rod, a fifth connecting rod, a sixth connecting rod, and a seventh connecting rod; the first connecting rod and the second connecting rod are hinged to each other, and a hinged end between the first connecting rod and the second connecting rod is located between a first end and a second end of the first connecting rod and located between a first end and a second end of the second connecting rod, so that the first connecting rod and the second connecting rod form an X-shaped scissor structure; the first ends of the first connecting rod and the second connecting rod are respectively hinged to the first tong arm and the second tong arm, and the second ends of the first connecting rod and the second connecting rod are respectively hinged to first ends of the third connecting rod and the fourth connecting rod; second ends of the third connecting rod and the fourth connecting rod are hinged to the swing seat, and axial directions of the third connecting rod and the fourth connecting rod hinged to the swing seat are identical; first ends of the fifth connecting rod and the sixth connecting rod are respectively hinged to the first tong arm and the second tong arm, second ends of the fifth connecting rod and the sixth connecting rod are hinged to a first end of the seventh connecting rod, and a second end of the seventh connecting rod is hinged to the first connecting rod and the second connecting rod at a hinged end between the first connecting rod and the second connecting rod; the swing seat is provided with a guide groove, and the guide groove is parallel to the first tong arm and the second tong arm; and the seventh connecting rod is arranged in the guide groove and can slide along the guide groove.

A plane in which the first tong arm and the second tong arm move relative to the swing seat and a rotation plane in which the swing seat rotates relative to the base are coplanar or perpendicular to each other.

The first tong arm is provided with a first linear binding part, and an opening of the first linear binding part faces the second tong arm; and the second tong arm is provided with a second linear binding part, and an opening of the second linear binding part faces the first tong arm.

The first tong arm is provided with a first fixing groove connected with the first linear binding part, and the second tong arm is provided with a second fixing groove connected with the second linear binding part.

At least two first fixing grooves are provided, and at least two second fixing grooves are provided.

The first tong arm is provided with a first notch, and the first notch is arranged at a tail end of the first tong arm; and the second tong arm is provided with a second notch, and the second notch is arranged at a tail end of the second tong arm.

A delivery apparatus provided by the present disclosure includes a controller and the above delivery actuator.

The controller includes a first control mechanism, and the first control mechanism is connected with a control end of the connecting rod mechanism of the delivery actuator; and the first control mechanism includes a first connecting line and a first coiling element, and the first connecting line is wound on the first coiling element and is connected with the control end.

A first end of the first connecting line is connected with a stop block, the stop block abuts against a fixing hole arranged on the swing seat so as to be fixed, and the first connecting line passes through the fixing hole and is wound around the control end, so that the first connecting line forms a pulley structure at the control end.

The delivery apparatus further includes a second control mechanism, and the second control mechanism is connected with the swing seat and is configured to control a rotation of the swing seat relative to the base.

The second control mechanism includes a second coiling element and at least two second connecting lines, first ends of the at least two second connecting lines are respectively connected to a first side and a second side of the swing seat, and the first side and the second side of the swing seat are two sides of a hinged end between the swing seat and the base located on a rotation path; a second end of the second connecting line is wound on the second coiling element; or the second control mechanism includes a connecting rod, a first end of the connecting rod is connected with the swing seat, a joint between the connecting rod and the swing seat is located outside a hinge shaft between the swing seat and the base, and a second end of the connecting rod is connected to a hand-held operating part arranged at a rear end of the delivery apparatus.

The swing seat is provided with a fixing part; the delivery apparatus includes a third connecting line, and the third connecting line includes a first sub-control line and a second sub-control line; the first sub-control line and the second sub-control line respectively include a binding part, a control part, and a connecting part for connecting the binding part and the control part; an implant is movably bound to the first tong arm by the binding part of the first sub-control line, the control part of the first sub-control line is connected and fixed to the fixing part of the swing seat, and the control part of the first sub-control line is configured to be triggered to unbind the binding part of the first sub-control line; and the implant is movably bound to the second tong arm by the binding part of the second sub-control line, the control part of the second sub-control line is connected and fixed to the fixing part of the swing seat, and the control part of the second sub-control line is configured to be triggered to unbind the binding part of the second sub-control line.

The swing seat is provided with a plurality of line grooves, and tail ends of at least some line grooves are provided with opening parts.

Compared with the prior art, the above delivery actuator and delivery apparatus provided in the embodiments of the present disclosure have the following advantages:

In the delivery actuator provided in the embodiment of the present disclosure, according to the connecting rod mechanism, the hinged end between the first connecting rod and the second connecting rod serves as the control end; the hinged end between the first connecting rod and the first tong arm serves as a first front connecting end, and the hinged end between the fifth connecting rod and the first tong arm serves as a first rear connecting end; the hinged end between the second connecting rod and the second tong arm serves as a second front connecting end, and the hinged end between the sixth connecting rod and the second tong arm serves as a second rear connecting end; and the connecting end among the third connecting rod and the fourth connecting rod and the swing seat as well as the first end and second end of the seventh connecting rod serve as third connecting ends. By using the control mechanism connected with the control end to control the control end, the first front connecting end and the first rear connecting end act on the first tong arm, and the second front connecting end and the second rear connecting end act on the second tong arm, so that the first tong arm and the second tong arm can be clamped or opened in parallel. Moreover, the above connecting rod mechanism has a simple structure and is relatively easy to operate to open and close the first tong arm and the second tong arm in parallel.

The delivery apparatus provided in the embodiment of the present disclosure includes the above delivery actuator, and has the same beneficial effects as the above delivery actuator, which will not be described here.

BRIEF DESCRIPTION OF THE DRAWINGS

Accompanying drawings herein are incorporated into the specification and constitute a part of the specification, show embodiments that conform to the present disclosure, and are used for explaining the principle of the present disclosure together with the specification.

In order to more clearly illustrate the technical solutions in the embodiments of the present disclosure or in the prior art, the accompanying drawings required for descriptions in the embodiments or the prior art will be briefly introduced below. Apparently, those of ordinary skill in the art can also obtain other accompanying drawings from these accompanying drawings without creative efforts.

In the figures.

Figure 1:
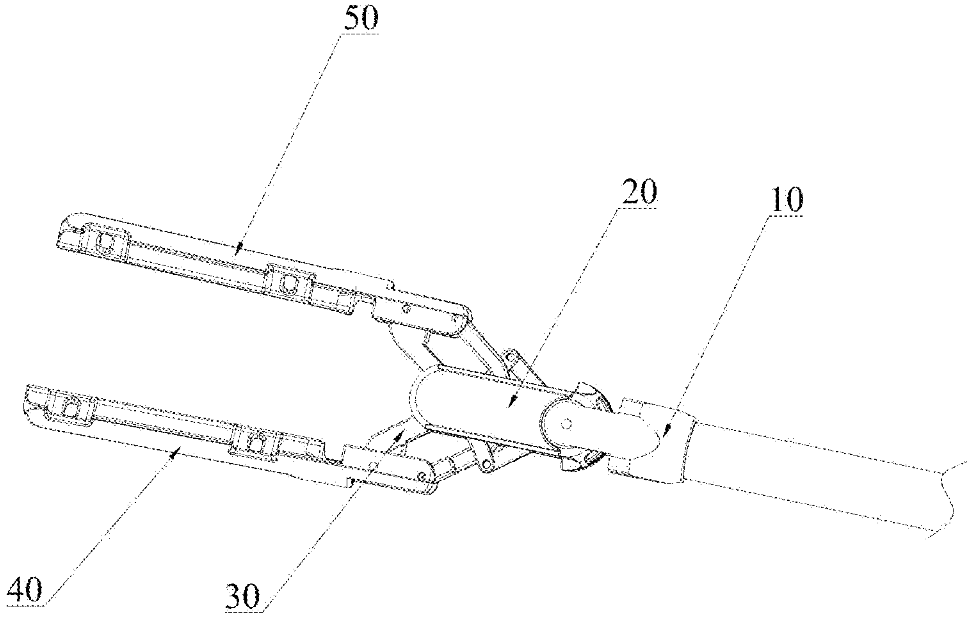
FIG. 1 is a schematic diagram of a delivery actuator provided in an embodiment of the present disclosure in an open state.
Figure 2:
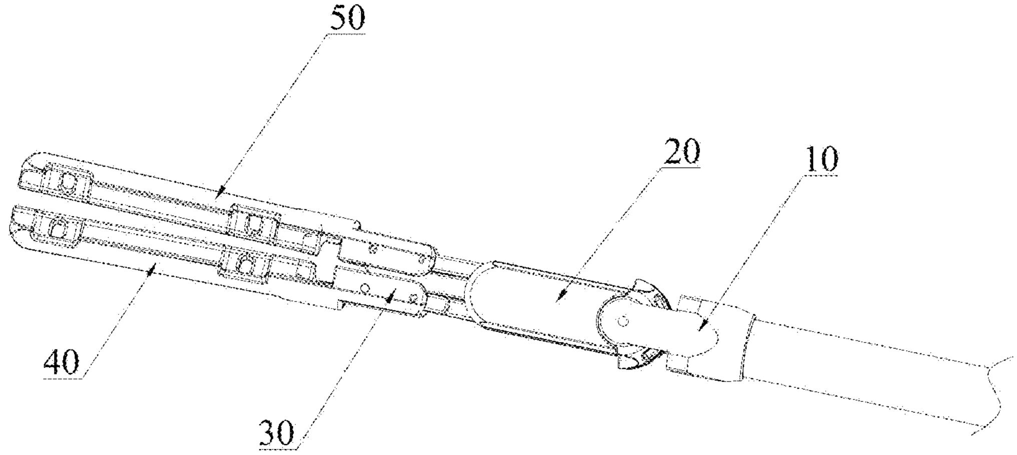
FIG. 2 is a schematic diagram of the delivery actuator shown in FIG. 1 in a closed state.

10—base;

20—swing seat;

201—guide groove; 202—fixing hole; 203, 203*a*, 203*b*, 203*c*, 203*d*, 203*e*—line groove; 204—stop block; 205—stop block; 206—connecting rod;

2031—main body part; 2032—opening part;

30—connecting rod mechanism;

301—first connecting rod; 301*a*—first end; 301*b*—second end;

302—second connecting rod; 302*a*—first end; 302*b*—second end;

303—third connecting rod; 303*a*—first end; 303*b*—second end;

304—fourth connecting rod; 304*a*—first end; 304*b*—second end;

305—fifth connecting rod; 305*a*—first end; 305*b*—second end;

306—sixth connecting rod; 306*a*—first end; 306*b*—second end;

307—seventh connecting rod; 307*a*—first end; 307*b*—second end;

40—first tong arm;

401—first linear binding part; 402—first fixing groove; 403—first notch;

50—second tong arm;

501—second linear binding part; 502—second fixing groove; 503—second notch;

60—first coiling element; 70—second coiling element;

A1—first front connecting end; A2—first rear connecting end; B1—second front connecting end; B2—second rear connecting end; C—third connecting end; D—control end; M—implant.

DETAILED DESCRIPTION OF THE EMBODIMENTS

To make the objectives, technical solutions, and advantages of the embodiments of the present disclosure clearer, the following clearly and completely describes the technical solutions in the embodiments of the present disclosure with reference to the accompanying drawings in the embodiments of the present disclosure. It is apparent that the described embodiments are some of rather than all the embodiments of the present disclosure. All other embodiments obtained by those of ordinary skill in the art based on the embodiments in the present disclosure without creative efforts shall fall within the scope of protection of the present disclosure.

The embodiments of a delivery actuator and a delivery apparatus provided by the present disclosure are described below with reference to the accompanying drawings.

(1) Embodiment of Delivery Actuator

Referring to FIG. 1 to FIG. 4, a delivery actuator provided in this embodiment is mounted at a front end of a delivery apparatus, and is configured to connect and fix an implant M to be delivered. For example, the implant M delivered by the delivery apparatus can be an auricle clamp. Taking the auricle clamp as an example, after the auricle clamp is fixed to the delivery actuator, the delivery apparatus is operated to enable the delivery actuator to enter the target position inside the human body, namely the left auricle. At the target position, the auricle clamp closes the left auricle, and then, the connection and fixation between the delivery actuator and the auricle clamp are released, so as to release the auricle clamp from the delivery actuator. Finally, the delivery apparatus is operated to remove the delivery actuator from the human body.

Generally, the delivery apparatus includes a hand-held operating part and a delivery actuator, as well as a connecting part for connecting the hand-held operating part with the delivery actuator. As mentioned above, the delivery actuator is configured to fix an implant such as an auricle clamp. The hand-held operating part is configured to grip and control components such as the delivery actuator during use. The delivery actuator extends into the human body during use while the hand-held operating part is located outside the human body. The connecting part is generally a rod-shaped structure or a tubular structure, and two ends of the connecting part are respectively connected with the delivery actuator and the hand-held operating part directly, or connected with the delivery actuator and the hand-held operating part through accessories such as corresponding connectors. In this embodiment, the direction of the delivery actuator relative to the hand-held operating part is referred to as the front, and the direction of the hand-held operating part relative to the delivery actuator is referred to as the rear. In the description of the solution of the present disclosure, a head end, a front end and other orientation words with similar meanings indicate that the component defined by the orientation word is located on a front side of a reference object, and a tail end, a rear end and other orientation words with similar meanings indicate that the component defined by the orientation word is located on a rear side of the reference object.

In this embodiment, as shown in FIG. 1 to FIG. 4, the delivery actuator includes a base 10, a swing seat 20, a connecting rod mechanism 30, a first tong arm 40, and a second tong arm 50. The swing seat 20 is connected to the base 10 and is rotatably connected to the base 10. Specifically, the base 10 can be fixedly connected with the connecting part at a front side of the connecting part.

Figure 5:
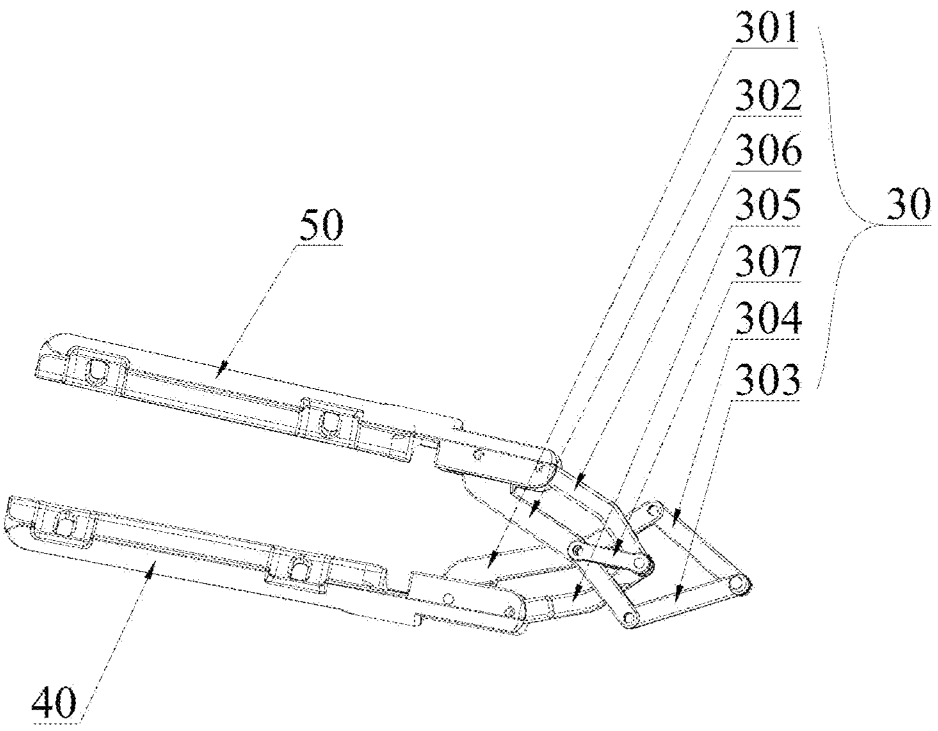
FIG. 5 is a schematic structural diagram of a connecting rod mechanism and a first tong arm and a second tong arm in the delivery actuator shown in FIG. 1.
Figure 6:
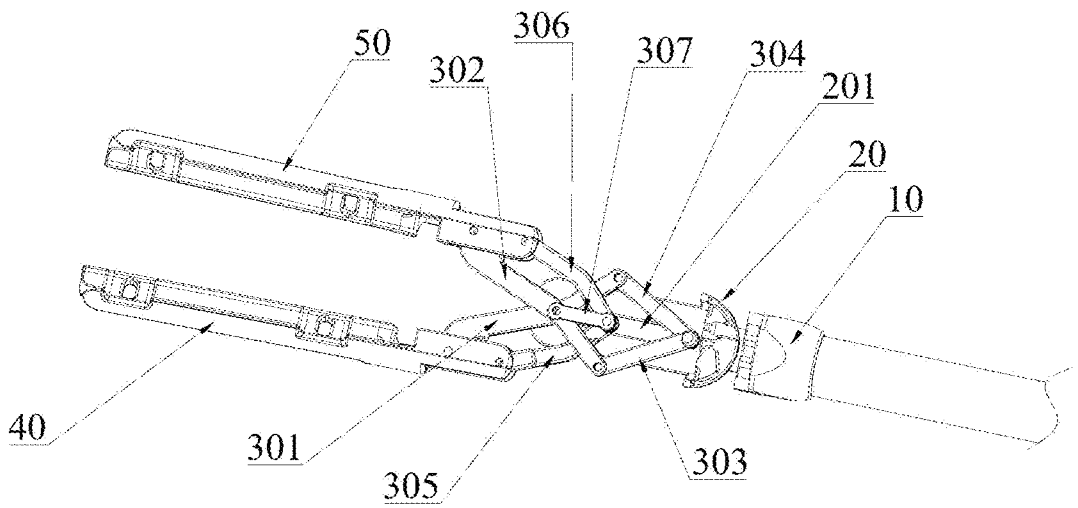
FIG. 6 is a schematic diagram of the connection relationship between the connecting rod mechanism and a swing seat as well as the first tong arm and the second tong arm in the delivery actuator shown in FIG. 1.
Figure 7:
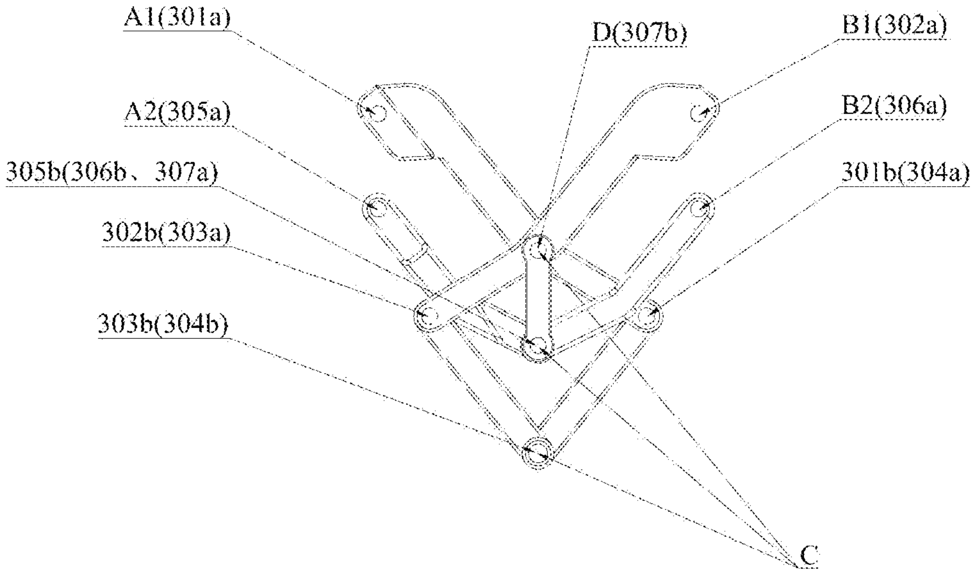
FIG. 7 is a schematic structural diagram of the connecting rod mechanism in the delivery actuator shown in FIG. 1.

As shown in FIG. 5 to FIG. 7, the connecting rod mechanism 30 has a first front connecting end A1, a first rear connecting end A2, a second front connecting end B1, a second rear connecting end B2, third connecting ends C, and a control end D, wherein the control end D is connected with a control mechanism, the first front connecting end A1 and the first rear connecting end A2 are respectively connected to the first tong arm 40 at two positions along a head-to-tail direction on the first tong arm 40, the second front connecting end B1 and the second rear connecting end B2 are respectively connected to the second tong arm 50 at two positions along a head-to-tail direction on the second tong arm 50, and the third connecting ends C are connected with the swing seat 20. The connecting rod mechanism 30 can respond to the control mechanism connected with the control end D to control the control end D, the first front connecting end A1 and the first rear connecting end A2 act on the first tong arm 40, and the second front connecting end B1 and the second rear connecting end B2 act on the second tong arm 50, so that the first tong arm 40 and the second tong arm 50 can be clamped or opened in parallel.

The connecting rod mechanism 30 has the first front connecting end A1 and first rear connecting end A2 connected with the first tong arm 40, based on the two connecting ends, the connecting rod mechanism 30 can apply equivalent or corresponding acting forces to two positions on the first tong arm 40, and the acting forces are applied towards or away from the second tong arm 50, so that the first tong arm 40 can move towards or away from the second tong arm 50 in a translational manner to maintain the angle between the first tong arm 40 and the second tong arm 50 unchanged during this process. Similarly, the connecting rod mechanism 30 has the second front connecting end B1 and second rear connecting end B2 connected with the second tong arm 50, based on the two connecting ends, the connecting rod mechanism 30 can apply equivalent or corresponding acting forces to two positions on the second tong arm 50, and the acting forces are applied towards or away from the first tong arm 40, so that the second tong arm 50 can move towards or away from the first tong arm 40 in a translational manner to maintain the angle between the second tong arm 50 and the first tong arm 40 unchanged during this process. Therefore, based on the above two aspects, by arranging the control mechanism to apply appropriate acting force to the control end D, the connecting rod mechanism 30 can control the first tong arm 40 and the second tong arm 50 to move close to or away from each other in parallel, so as to enable the first tong arm 40 and the second tong arm 50 to tend towards a closed state or an open state.

Specifically, as shown in FIG. 5 to FIG. 7, the connecting rod mechanism 30 includes a first connecting rod 301, a second connecting rod 302, a third connecting rod 303, a fourth connecting rod 304, a fifth connecting rod 305, a sixth connecting rod 306, and a seventh connecting rod 307.

Figure 8:
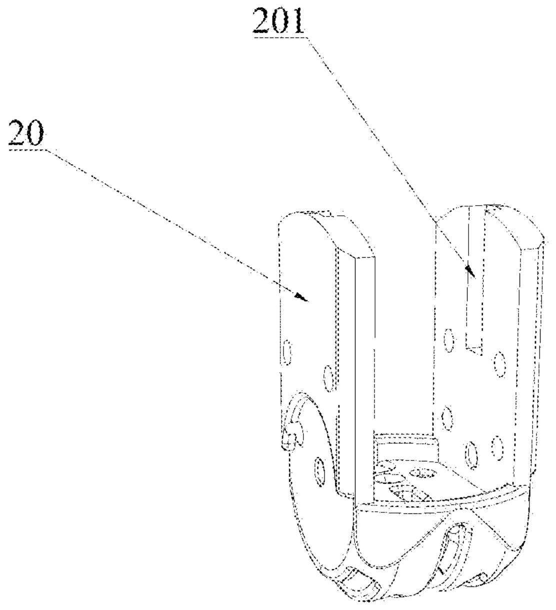
FIG. 8 is a schematic structural diagram of the swing seat in the delivery actuator shown in FIG. 1.

The first connecting rod 301 and the second connecting rod 302 are hinged to each other, and a hinged end between the first connecting rod 301 and the second connecting rod 302 is located between a first end 301*a* and a second end 301*b* of the first connecting rod 301 and located between a first end 302*a* and a second end 302*b* of the second connecting rod 302, so that the first connecting rod 301 and the second connecting rod 302 form an X-shaped scissor structure. The first end 301*a* of the first connecting rod 301 and the first end 302*a* of the second connecting rod 302 are respectively hinged to the first tong arm 40 and the second tong arm 50, and the second end 301*b* of the first connecting rod 301 and the second end 302*b* of the second connecting rod 302 are respectively hinged to a first end 304*a* of the fourth connecting rod 304 and a first end 303*a* of the third connecting rod 303; and a second end 303*b* of the third connecting rod 303 and a second end 304*b* of the fourth connecting rod 304 are hinged to the swing seat 20, and axial directions of the third connecting rod 303 and the fourth connecting rod 304 hinged to the swing seat 20 are identical. A first end 305*a* of the fifth connecting rod 305 and a first end 306*a* of the sixth connecting rod 306 are respectively hinged to the first tong arm 40 and the second tong arm 50, a second end 305*b* of the fifth connecting rod 305 and a second end 306*b* of the sixth connecting rod 306 are hinged to a first end 307*a* of the seventh connecting rod 307, and a second end 307*b* of the seventh connecting rod 307 is hinged to the first connecting rod 301 and the second connecting rod 302 at the hinged end between the first connecting rod 301 and the second connecting rod 302. As shown in FIG. 8, the swing seat 20 is provided with a guide groove 201, and the guide groove 201 is parallel to the first tong arm 40 and the second tong arm 50; and the seventh connecting rod 307 is arranged in the guide groove 201 and can slide along the guide groove 201.

As shown in FIG. 7, the hinged end between the first connecting rod 301 and the second connecting rod 302 is the control end D. The hinged end between the first connecting rod 301 and the first tong arm 40, namely the first end 301*a* of the first connecting rod 301 is the first front connecting end A1, and the hinged end between the fifth connecting rod 305 and the first tong arm 40, namely the first end 305*a* of the fifth connecting rod 305 is the first rear connecting end A2. The hinged end between the second connecting rod 302 and the second tong arm 50, namely the first end 302*a* of the second connecting rod 302 is the second front connecting end B1, and the hinged end between the sixth connecting rod 306 and the second tong arm 50, namely the first end 306*a* of the sixth connecting rod is the second rear connecting end B2. The third connecting ends C include the connecting end among the third connecting rod 303 and fourth connecting rod 304 and the swing seat 20, namely the second end 303*b* of the third connecting rod 303 and the second end 304*b* of the fourth connecting rod 304, and further include the first end 307*a* and second end 307*b* of the seventh connecting rod 307.

As for the connecting rod mechanism 30 in the embodiment, when the control mechanism applies a rearward pulling force towards the tail end of the delivery actuator from the rear side of the control end D to the control end D, because the second end 303*b* of the third connecting rod 303 and the second end 304*b* of the fourth connecting rod 304 are hinged to the swing seat 20, there positions are fixed. In a four-connecting rod mechanism composed of four connecting ends, namely the second end 301*b* of the first connecting rod 301 (the first end 304*a* of the fourth connecting rod 304), the second end 302*b* of the second connecting rod 302 (the first end 303*a* of the third connecting rod 303), the second end 303*b* of the third connecting rod 303 (the second end 304*b* of the fourth connecting rod 304), and the hinged end between the first connecting rod 301 and the second connecting rod 302, the second end 301*b* of the first connecting rod 301 (the first end 304*a* of the fourth connecting rod 304) and the second end 302*b* of the second connecting rod 302 (the first end 303*a* of the third connecting rod 303) will move outward and move away from each other; and the hinged end between the first connecting rod 301 and the second connecting rod 302 will move towards the second end 303*b* of the third connecting rod 303 (the second end 304*b* of the fourth connecting rod 304), and the two will move close to each other. Correspondingly, the first end 301*a* of the first connecting rod 301 and the first end 302*a* of the second connecting rod 302 will also move away from each other. That is, at the first front connecting end A1, the first tong arm 40 will be subjected to an acting force in the direction away from the second tong arm 50, tending to move away from the second tong arm 50; and at the second front connecting end B1, the second tong arm 50 will be subjected to an acting force in the direction away from the first tong arm 40, tending to move away from the first tong arm 40.

A four-connecting rod mechanism in the shape of a parallelogram is formed among the first end 301*a* of the first connecting rod 301, the first end 305*a* of the fifth connecting rod 305, the first end 307*a* of the seventh connecting rod 307 (the hinged end between the fifth connecting rod 305 and the sixth connecting rod 306), and the second end 307*b* of the seventh connecting rod 307 (the hinged end between the first connecting rod 301 and the second connecting rod 302). In a case that the seventh connecting rod 307 is constrained by the guide groove 201 on the swing seat 20 and can only move along the guide groove 201 towards the tail end direction of the delivery actuator, the first connecting rod 301 drives the first tong arm 40 to move towards the direction away from the second tong arm 50 at the first end 301*a*, namely the first front connecting end A1. During the movement process, the above four-connecting rod mechanism will maintain the shape of the parallelogram, so that at the first rear connecting end A2, the first tong arm 40 will also move towards the direction away from the second tong arm 50 to maintain the parallel state between the first tong arm 40 and the seventh connecting rod 307.

Similarly, a four-connecting rod mechanism in the shape of a parallelogram is also formed among the first end 302*a* of the second connecting rod 302, the first end 306*a* of the sixth connecting rod 306, the first end 307*a* of the seventh connecting rod 307 (the hinged end between the fifth connecting rod 305 and the sixth connecting rod 306), and the second end 307*b* of the seventh connecting rod 307 (the hinged end between the first connecting rod 301 and the second connecting rod 302). The second connecting rod 302 drives the second tong arm 50 to move towards the direction away from the first tong arm 40 at the first end 302*a*, namely the second front connecting end B1. During the movement process, the above four-connecting rod mechanism will maintain the shape of the parallelogram, so that at the second rear connecting end B2, the second tong arm 50 will also move towards the direction away from the first tong arm 40 to maintain the parallel state between the second tong arm 50 and the seventh connecting rod 307.

Therefore, according to the above, by applying a rearward pulling force to the control end D through the control mechanism, the first tong arm 40 and the second tong arm 50 can be moved away from each other in parallel, tending towards an open state.

On the contrary, when the control mechanism no longer applies the pulling force to the control end D from the rear side of the control end D, the control mechanism releases the control end D. In this case, an implant connected and fixed to the first tong arm 40 and the second tong arm 50 of the delivery actuator can apply acting forces facing each other to the first tong arm 40 and the second tong arm 50 (for example, specifically can be implemented by arranging an elastic component in a stretched state on the implant). Under the acting forces, the first tong arm 40 and the second tong arm 50 tend to move close to each other and transition to a closed state. The process of transitioning to the closed state is similar to the above process of transitioning the first tong arm 40 and the second tong arm 50 to the open state, and the process will not be repeated here. The finally implemented state is that the seventh connecting rod 307 moves along the guide groove 201 on the swing seat 20 to the initial position in the forward direction.

Figure 14:
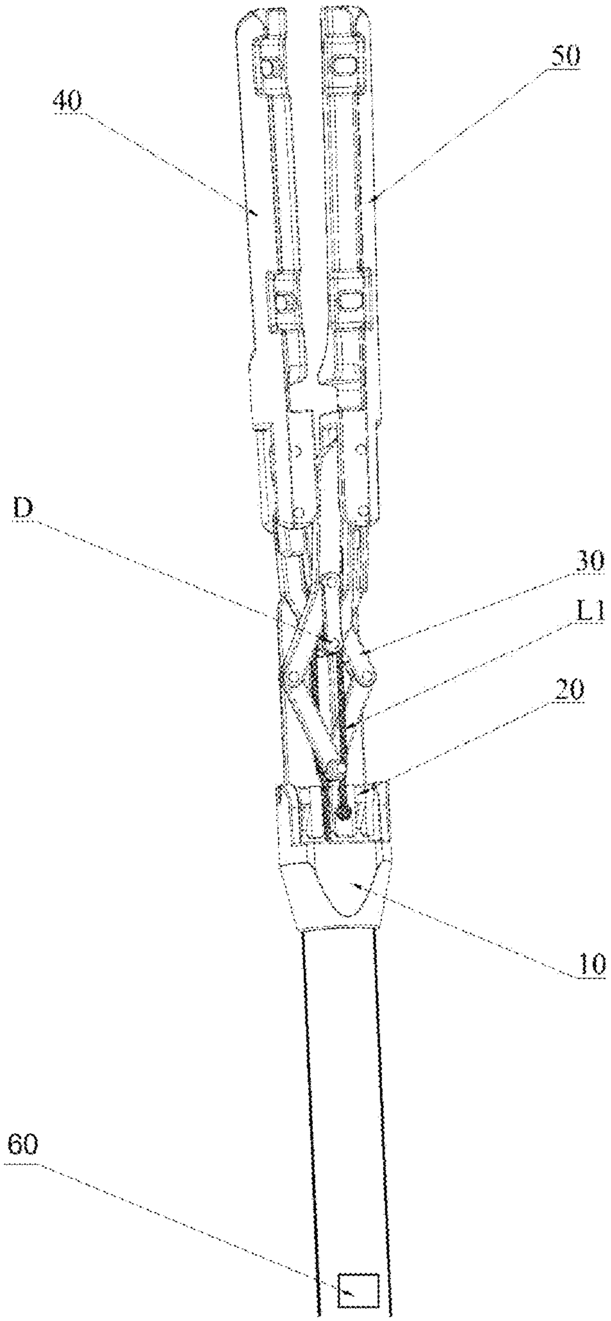
FIG. 14 is a schematic diagram of a control mode of a first control mechanism.

By means of the seventh connecting rod 307, the second end of the seventh connecting rod 307 is actually the hinged end between the first connecting rod 301 and the second connecting rod 302, and the first end of the seventh connecting rod 307 is actually the hinged end between the fifth connecting rod 305 and the sixth connecting rod 306. As shown in FIG. 14, with reference to FIG. 7, in other implementation solutions of the delivery actuator, the hinged end between the fifth connecting rod 305 and the sixth connecting rod 306 can also be used as the control end D, which is equivalent to the above implementation solution using the hinged end between the first connecting rod 301 and the second connecting rod 302 as the control end D.

In this embodiment, the swing seat 20 rotates in a plane relative to the base 10, rather than freely swings in a three-dimensional space. Thus, for the swing seat 20, fewer control components are required for controlling the rotation of the swing seat 20 relative to the base 10, so that the device cost can be reduced. Furthermore, there are also fewer control nodes for controlling the rotation of the swing seat 20 relative to the base 10, so that the probability of faults occurring during the control process can be reduced, and the reliability of movement control can be improved.

Moreover, the connecting rod mechanism 30 in this embodiment is simple in structure and smaller in volume, a larger operating space is not required for enabling the first tong arm 40 and the second tong arm 50 to move close to or away from each other in parallel, and the operating difficulty can be reduced when the implant is delivered.

Referring to FIG. 1 to FIG. 4, a plane in which the first tong arm 40 and the second tong arm 50 move relative to the swing seat 20 and a rotation plane in which the swing seat 20 rotates relative to the base 10 are coplanar to each other. In other words, the two planes are essentially one plane, and the rotations of the first tong arm 40 and the second tong arm 50 relative to the swing seat 20 and the rotation of the swing seat 20 relative to the base 10 are movements in the same plane.

In this embodiment, the plane in which the first tong arm 40 and the second tong arm 50 relatively move relative to the swing seat 20 and the plane in which the swing seat 20 rotates relative to the base 10 are the same plane. This arrangement facilitates the movement of the implant to a target position in one plane, and at the target position, the first tong arm 40 and the second tong arm 50 are closed or opened in the same plane. In general, the direction of movement of the implant at the target position is determined. Based on the determined movement direction, because the rotation direction of the swing seat 20 relative to the base 10 is related to the above determined movement direction, when the swing seat 20 is controlled to rotate relative to the base 10, the above determined movement direction can be used as a reference, thereby facilitating the accurate control of the rotation of the swing seat 20 relative to the base 10, and facilitating the accurate movement of the first tong arm 40 and the second tong arm 50 and the implant fixed thereon to the target position.

Figure 9:
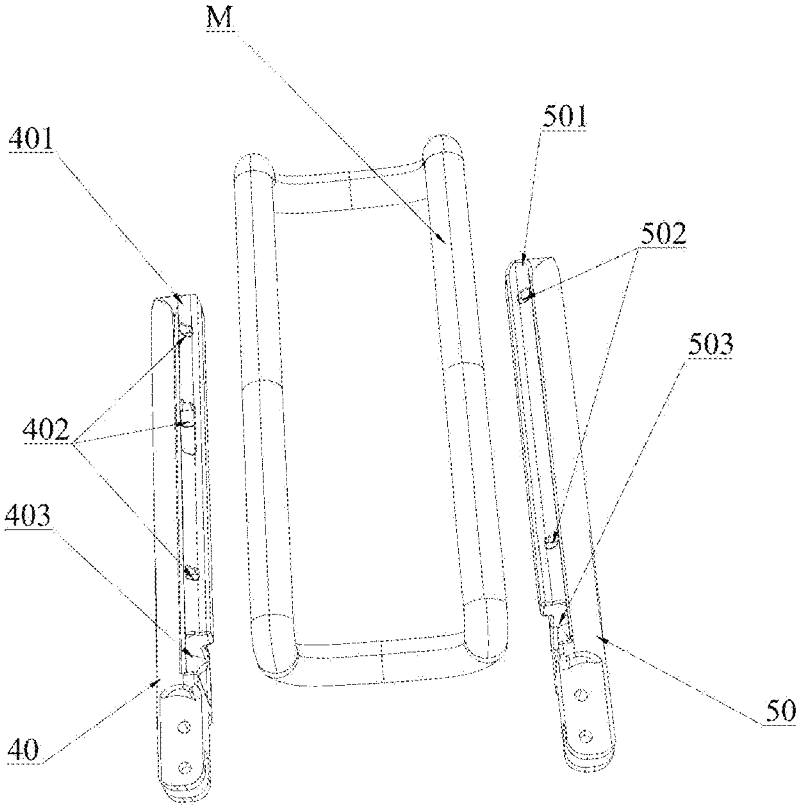
FIG. 9 is a schematic structural diagram of the first tong arm and the second tong arm in the delivery actuator shown in FIG. 1.
Figure 10:
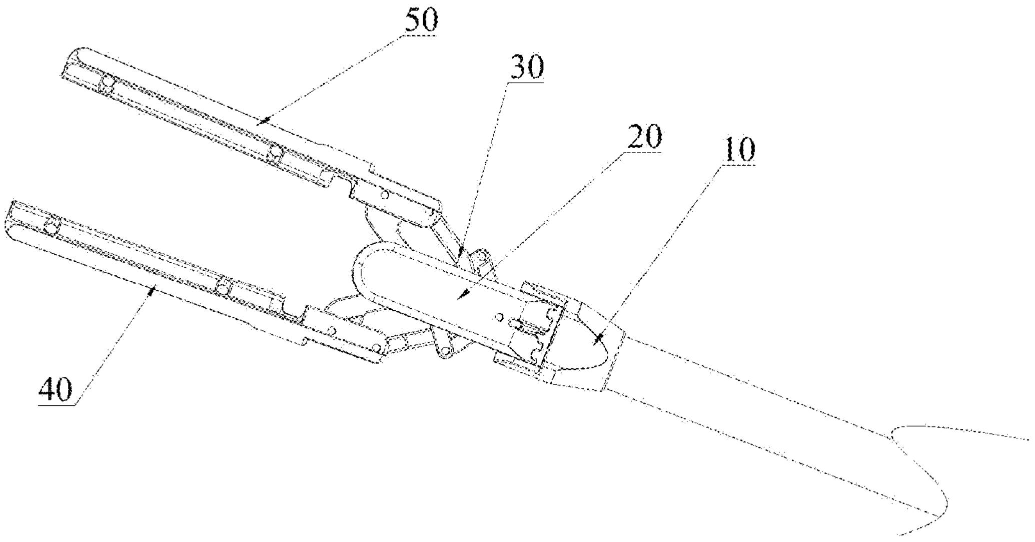
FIG. 10 is a schematic diagram of a delivery actuator provided in a modified embodiment of the embodiment of the present disclosure in an open state.
Figure 11:
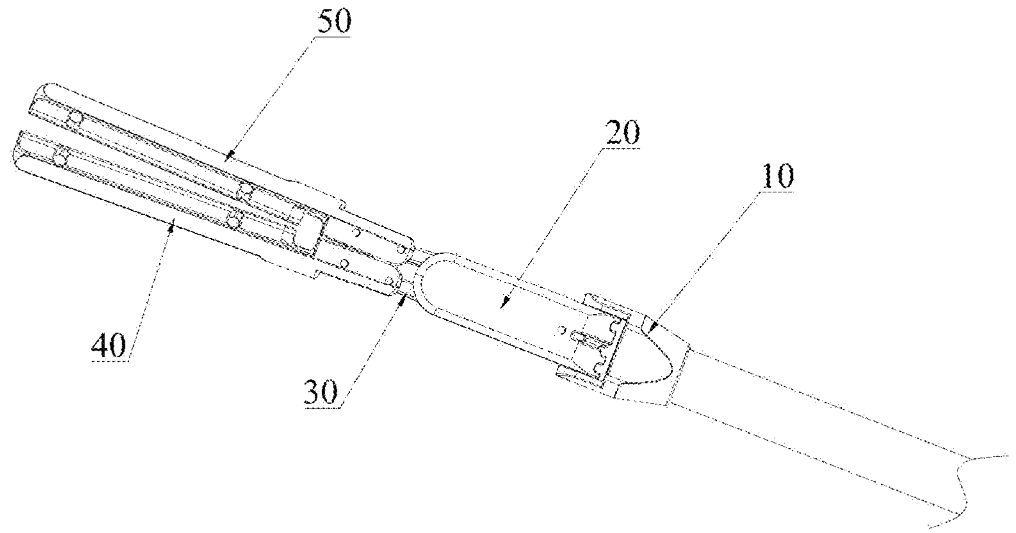
FIG. 11 is a schematic diagram of the delivery actuator shown in FIG. 10 in a closed state.
Figure 12:
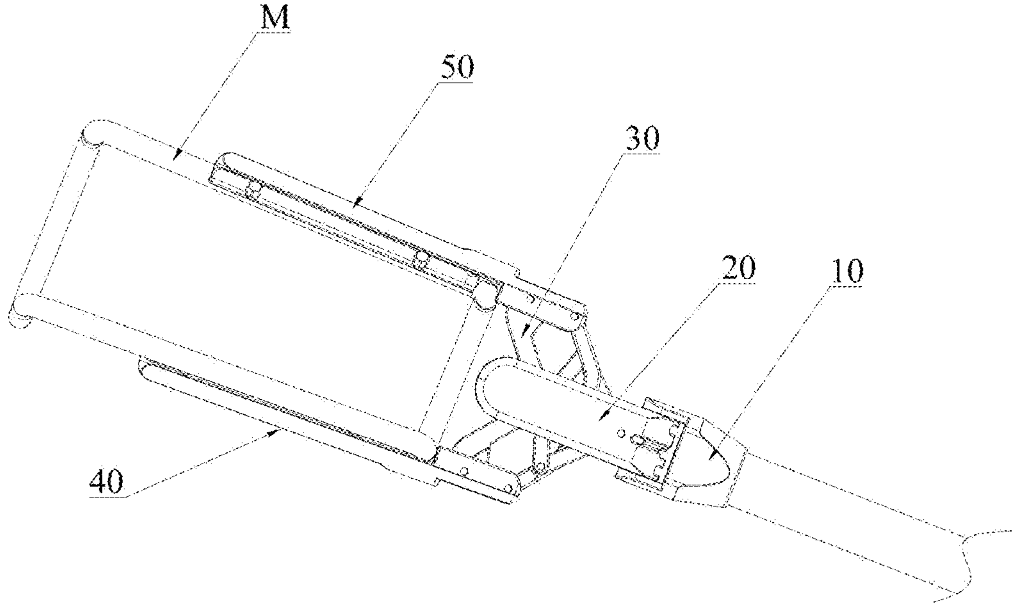
FIG. 12 is a schematic diagram of the delivery actuator shown in FIG. 10 connected with an implant and in an open state.
Figure 13:
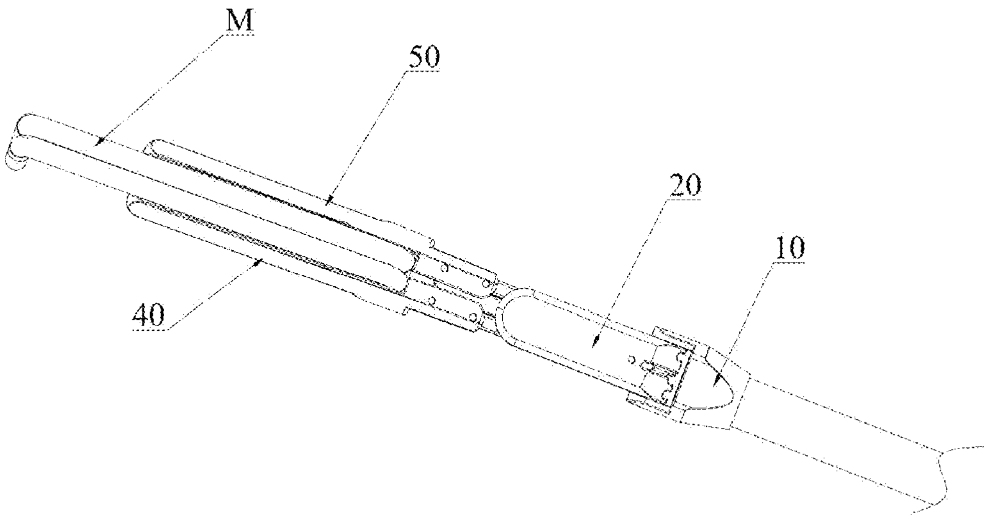
FIG. 13 is a schematic diagram of the delivery actuator shown in FIG. 10 connected with an implant and in a closed state.

In this embodiment, as shown in FIG. 9, the first tong arm 40 is provided with a first linear binding part 401, and an opening of the first linear binding part 401 faces the second tong arm 50. The first linear binding part 401 can be used for binding a clamp arm of an implant M such as an auricle clamp, and the clamp arm of the implant M can be fixed in the first linear binding part 401 by using lines meeting certain requirements between the first linear binding part 401 and the clamp arm of the implant M. The second tong arm 50 is provided with a second linear binding part 501, and an opening of the second linear binding part 501 faces the first tong arm 40. The second linear binding part 501 can be used for binding a clamp arm of an implant M such as an auricle clamp, and the clamp arm of the implant M can be fixed in the second linear binding part 501 by using lines meeting certain requirements between the second linear binding part 501 and the clamp arm of the implant M.

The first linear binding part 401 and the second linear binding part 501 are configured to be connected with the implant M so as to connect and fix the implant M to the delivery actuator. Taking the implant M being an auricle clamp as an example, the first linear binding part 401 and the second linear binding part 501 are respectively connected with two clamp arms of the auricle clamp so as to fix the auricle clamp to the delivery actuator. After the auricle clamp is fixed to the delivery actuator, the opening and closing of the first tong arm 40 and the second tong arm 50 can drive the two clamp arms of the auricle clamp to move close to or away from each other in parallel. At the target position, the left auricle can be clamped and closed with the parallel approach of the first tong arm 40 and the second tong arm 50.

The shapes of the first linear binding part 401 and the second linear binding part 501 can be linear grooves corresponding to the shapes of the clamp arms of the implant M, and the clamp arms of the implant M and the linear grooves are connected and fixed together based on the corresponding relationship between the shapes. The first linear binding part 401 and the second linear binding part 501 can also be non-groove structures such as planar structures, and the clamp arms of the implant M are bound and fixed through lines at the non-groove structures such as the planar structures.

Specifically, the first tong arm 40 is provided with a first fixing groove 402 connected with the first linear binding part 401. The first fixing groove 402 is configured to thread connecting lines to bind and fix the implant and the first linear binding part 401. The second tong arm 50 is provided with a second fixing groove 502 connected with the second linear binding part 501. The second fixing groove 502 is also configured to thread connecting lines to bind and fix the implant and the second linear binding part 501.

At least two first fixing grooves 402 are provided, and at least two second fixing grooves 502 are provided. By this arrangement, the first linear binding part 401 and the implant can be bound and fixed at the at least two positions of the first linear binding part 401, and the second linear binding part 501 and the implant can be bound and fixed at the at least two positions of the second linear binding part 501, so that the implant can be bound and fixed to the first linear binding part 401 and the second linear binding part 501 more firmly in the length direction of the first tong arm 40 and the second tong arm 50.

The first tong arm 40 is provided with a first notch 403, and the first notch 403 is arranged at a tail end of the first tong arm 40. The second tong arm 50 is provided with a second notch 503, and the second notch 503 is arranged at a tail end of the second tong arm 50. The first notch 403 and the second notch 503 are configured to accommodate protrusions of the implant facing the first tong arm 40 and the second tong arm 50. Taking the auricle clamp as an example, an elastic connecting part connected between the two clamp arms of the auricle clamp will protrude towards the direction of the first tong arm 40 and the second tong arm 50 at the junctions with the two clamp arms, and the first notch 403 and the second notch 503 can accommodate these parts, thereby avoiding interference between the auricle clamp and the first tong arm 40 as well as the second tong arm 50.

It should be noted that in terms of the implementation of the present disclosure, simple modifications can also be made on the basis of the above embodiments as alternative embodiments. In an alternative embodiment, as shown in FIG. 10 to FIG. 13, a plane in which the first clamp arm 40 and the second clamp arm 50 move relative to the swing seat 20 and a rotation plane in which the swing seat 20 rotates relative to the base 10 are perpendicular to each other, rather than coplanar generally as in Embodiment 1 mentioned above. However, the same as Embodiment 1 mentioned above, fewer control components are required for controlling the rotation of the swing seat 20 relative to the base 10, and there are also fewer control nodes for controlling the rotation of the swing seat 20 relative to the base 10. Moreover, the connecting rod mechanism 30 is also simple in structure and smaller in volume, a larger operating space is not required for enabling the first tong arm 40 and the second tong arm 50 to move close to or away from each other in parallel, and the operating difficulty can be reduced when the implant is delivered. Similar to Embodiment 1 mentioned above, an association relationship is also established between the direction of rotation of the swing seat 20 relative to the base 10 and the determined direction of movement of the implant at the target position. Based on the association relationship, when the swing seat 20 is controlled to rotate relative to the base 10, the above determined movement direction can be used as a reference, so as to accurately control the rotation of the swing seat 20 relative to the base 10, thereby facilitating the accurate movement of the first tong arm 40 and the second tong arm 50 and the implant fixed thereon to the target position.

In another alternative embodiment of the present disclosure, the structures of the first tong arm 40 and the second tong arm 50 can also be structures shown in FIG. 16 to FIG. 17 and FIG. 21 to FIG. 23. In the structures shown in FIG. 16 to FIG. 17 and FIG. 21 to FIG. 23, the first tong arm 40 and the second tong arm 50 are also provided with a first linear binding part 401 and a second linear binding part 501 for accommodating an implant M, as well as slots for fixing the implant M.

In still another alternative embodiment of the present disclosure, the connecting rod mechanism 30 can be different from the connecting rod mechanism in the above embodiments. As shown in FIG. 16 to FIG. 19, in this alternative embodiment, the connecting rod mechanism 30 includes a first connecting rod 301, a second connecting rod 302, a third connecting rod 303, a fourth connecting rod 304, a fifth connecting rod 305, and a sixth connecting rod 306. The first connecting rod 301 and the second connecting rod 302 are hinged to each other, and a hinged end between the first connecting rod 301 and the second connecting rod 302 is located between a first end 301*a* and a second end 301*b* of the first connecting rod 301 and located between a first end 302*a* and a second end 302*b* of the second connecting rod 302, so that the first connecting rod 301 and the second connecting rod 302 form an X-shaped scissor structure. A hinge shaft of the first connecting rod 301 and the second connecting rod 302 is hinged to the swing seat 20. The first ends 301*a* and 302*a* of the first connecting rod 301 and the second connecting rod 302 are respectively hinged to the first tong arm 40 and the second tong arm 50, and the second ends 301*b* and 302*b* of the first connecting rod 301 and the second connecting rod 302 are respectively hinged to first ends 303*a* and 304*a* of the third connecting rod 303 and the fourth connecting rod 304. Second ends 303*b* and 304*b* of the third connecting rod 303 and the fourth connecting rod 304 are hinged to each other. First ends 305*a* and 306*a* of the fifth connecting rod 305 and the sixth connecting rod 306 are respectively hinged to the first tong arm 40 and the second tong arm 50, second ends 305*b* and 306*b* of the fifth connecting rod 305 and the sixth connecting rod 306 are hinged to each other, and a hinge shaft of the fifth connecting rod 305 and the sixth connecting rod 306 is hinged to the swing seat 20. The swing seat 20 is provided with a guide groove 201, and the guide groove 201 is parallel to the first tong arm 40 and the second tong arm 50. A hinge shaft of the third connecting rod 303 and the fourth connecting rod 304 is arranged in the guide groove 201 and can slide along the guide groove 201. The hinged end between the third connecting rod 303 and the fourth connecting rod 304 serves as a control end D. The hinged end between the first connecting rod 301 and the first tong arm 40 serves as a first front connecting end A1, and the hinged end between the fifth connecting rod 305 and the first tong arm 40 serves as a first rear connecting end A2. The hinged end between the second connecting rod 302 and the second tong arm 50 serves as a second front connecting end B1, and the hinged end between the sixth connecting rod 306 and the second tong arm 50 serves as a second rear connecting end B2.

In this alternative embodiment, a forward force can be applied to the control end D (the force can be applied through a line structure such as a steel wire; specifically, the line structure such as the steel wire can be led out from a hand-held operating part at the rear end, and the line structure such as the steel wire is wound on the hinge shaft of the first connecting rod 301 and the second connecting rod 302 or the hinge shaft of the fifth connecting rod 305 and the sixth connecting rod 306, and returns to the control end D to be connected and fixed; in this way, the line structure such as the steel wire is pulled rearward at the hand-held operating part to act on the control end D to form a forward acting force), to control the first tong arm 40 and the second tong arm 50 to be opened. The pulling force on the control end D can be released to clamp the first tong arm 40 and the second tong arm 50. Specifically, when a forward pulling force is applied to the control end D, namely the hinged end between the third connecting rod 303 and the fourth connecting rod 304, the pulling force drives the hinged end between the first connecting rod 301 and the fourth connecting rod 304 and the hinged end between the second connecting rod 302 and the third connecting rod 303 to move forward and be opened outward first; the pulling force further acts on the hinged end between the first connecting rod 301 and the first tong arm 40 (the first front connecting end A1) and the hinged end between the second connecting rod 302 and the second tong arm 50 (the second front connecting end B1) to enable the two to be opened outward; and through the fifth connecting rod 305 and the sixth connecting rod 306, the pulling force synchronously drives the hinged end between the fifth connecting rod 305 and the first tong arm 40 (the first rear connecting end A2) and the hinged end between the sixth connecting rod 306 and the second tong arm 50 (the second rear connecting end B2) to enable the two to be opened outward, so that the first tong arm 40 and the second tong arm 50 are opened in parallel. When stopping applying the forward acting force to the control end D, the implant connected and fixed to the first tong arm 40 and the second tong arm 50 of the delivery actuator can apply acting forces facing each other to the first tong arm 40 and the second tong arm 50 (for example, specifically can be implemented by arranging an elastic component in a stretched state on the implant). Under the acting forces, the first tong arm 40 and the second tong arm 50 tend to move close to each other and transition to a closed state. The process of transitioning to the closed state is similar to the above process of transitioning the first tong arm 40 and the second tong arm 50 to the open state, and the process will not be repeated here.

In this embodiment, the connecting rod mechanism 30 is simple in structure, and the processes of opening and closing the first tong arm 40 and the second tong arm 50 in parallel are more simple and convenient. Compared with the above embodiments, the connecting rod mechanism in this embodiment has a better number of connecting rods. Moreover, in the connecting rod mechanism 30, the control end is located at a more rear position and thus is easier to control, and the processes of opening and closing are more simple, convenient, stable and reliable.

(2) Embodiment of Delivery Apparatus

In this embodiment, the delivery apparatus includes a controller and the delivery actuator described in the above embodiment of the delivery actuator.

The controller is configured to control the state between the first tong arm 40 and the second tong arm 50 of the delivery actuator and control the rotation of the swing seat 20 relative to the base 10, and is also configured to control the implant connected and fixed to the delivery actuator.

Specifically, the controller includes a first control mechanism, a second control mechanism, and a third control mechanism.

Based on the embodiment of the delivery actuator shown in FIG. 1 to FIG. 13, the first control mechanism is connected with the control end D of the connecting rod mechanism 30 of the delivery actuator. As shown in FIG. 14, the first control mechanism includes a first connecting line L1 and a first coiling element 60, and the first connecting line L1 is wound on the first coiling element and is connected with the control end D. Specifically, the first connecting line L1 can be a steel wire.

The first connecting line L1 is connected with the control end D. When the first connecting line L1 pulls the control end D to apply a rearward pulling force to the control end D, the pulling force acts on the connecting rod mechanism 30 to control the distance between the first tong arm 40 and the second tong arm 50 to increase, tending towards the open state. When the first connecting line releases the control end D and no longer applies the rearward pulling force to the control end D, under the action of the implant, the distance between the first tong arm 40 and the second tong arm 50 decreases, tending towards the closed state. The specific process is described in detail in the above embodiment of the delivery actuator, and will not be repeated.

The first coiling element can coil or release the first connecting line L1 in a manner such as rotation. When the first coiling element coils the first connecting line L1, the first connecting line L1 pulls the control end D to apply the rearward pulling force to the control end D. When the first coiling element releases the first connecting line L1, the first connecting line L1 correspondingly releases the control end D and no longer applies the rearward pulling force to the control end D.

The connection of the control end D of the first connecting line L1 specifically can be that one end of the first connecting line L1 can be directly connected with the hinged end between the first connecting rod 301 and the second connecting rod 302. In addition, it can also be that a first end of the first connecting line L1 is connected with a stop block 204, the stop block 204 abuts against a fixing hole 202 arranged on the swing seat 20 so as to be fixed, and the first connecting line L1 passes through the fixing hole 202 and is wound around the control end D, so that the first connecting line L1 forms a pulley structure at the control end D.

Figure 15:
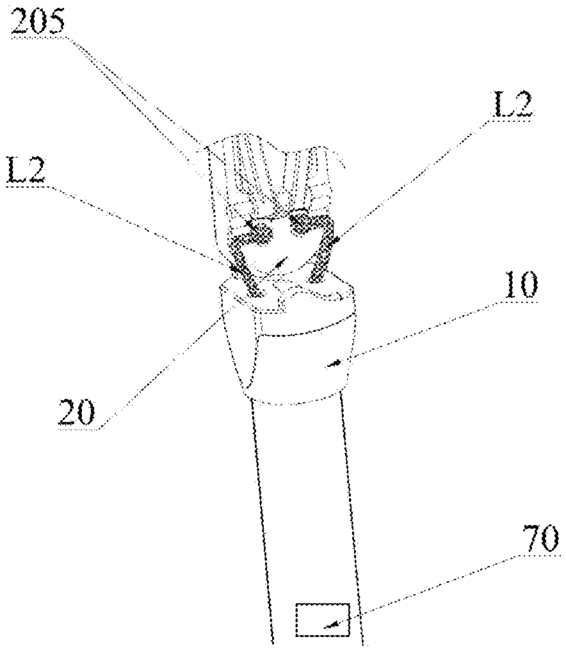
FIG. 15 is a schematic diagram of a control mode of a second control mechanism.
Figure 16:
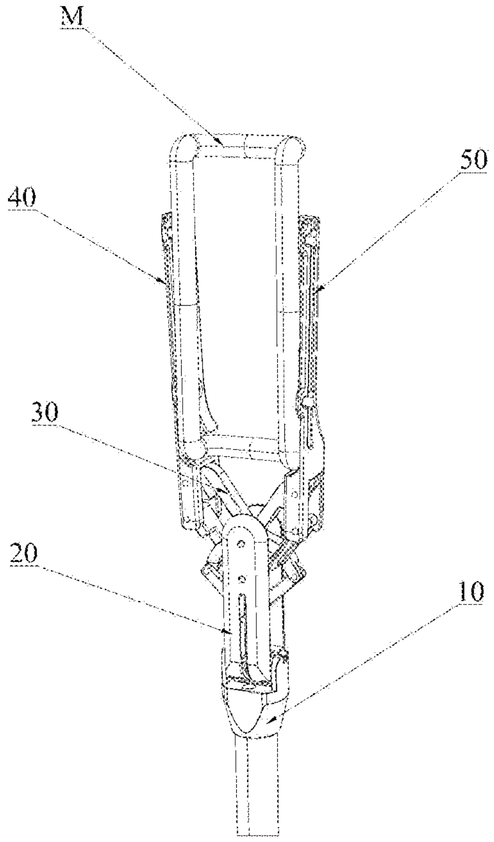
FIG. 16 is a schematic structural diagram of a delivery actuator in another embodiment of the present disclosure.
Figure 17:
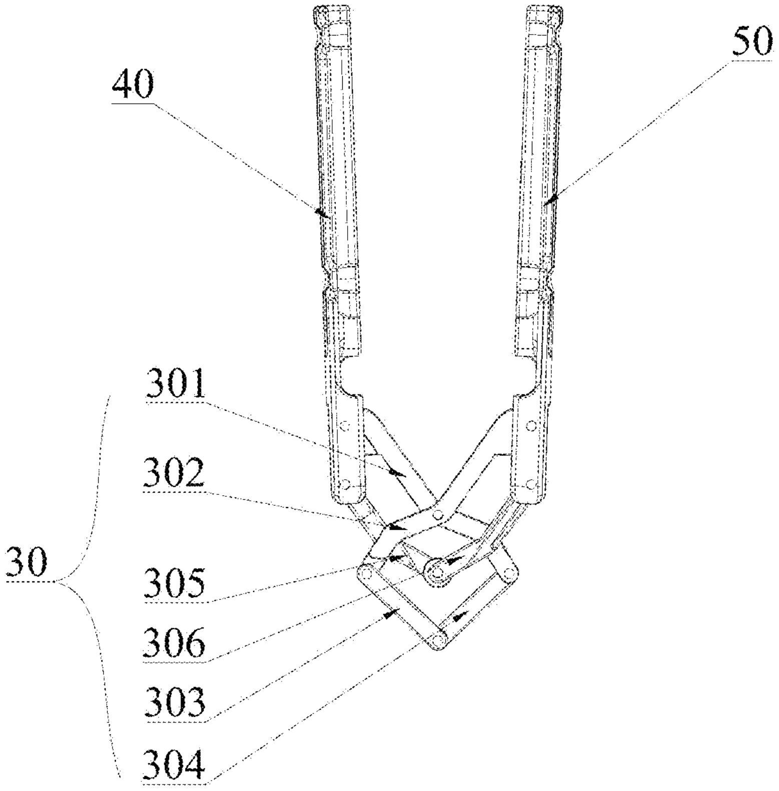
FIG. 17 is a schematic diagram of a connecting rod mechanism and a first tong arm and a second tong arm in the delivery actuator shown in FIG. 16.
Figure 18:
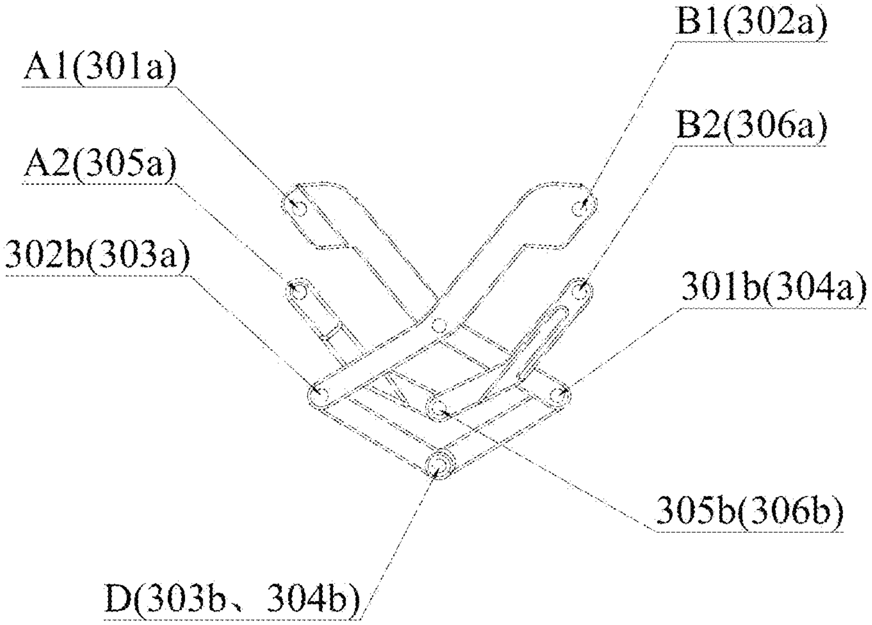
FIG. 18 is a schematic structural diagram of the connecting rod mechanism in the delivery actuator shown in FIG. 16.
Figure 19:
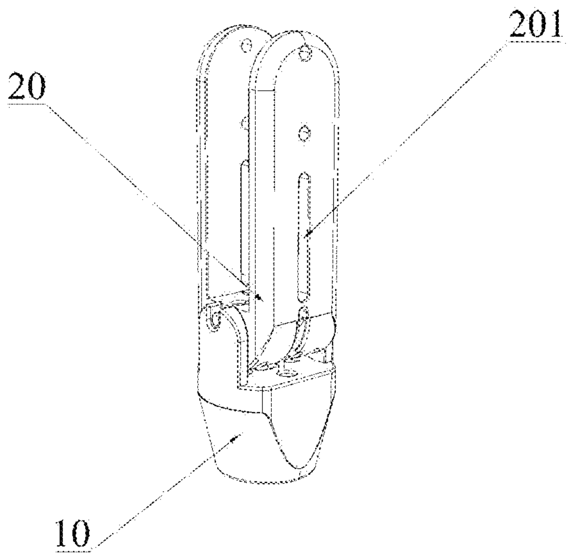
FIG. 19 is a schematic structural diagram of a swing seat and a base in the delivery actuator shown in FIG. 16.
Figure 20:
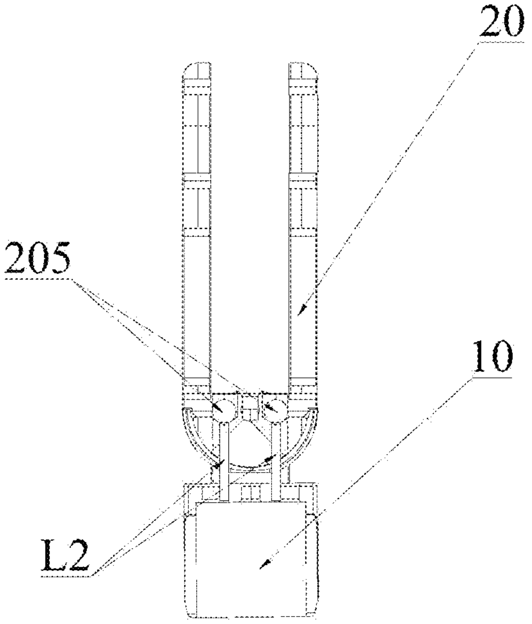
FIG. 20 is a schematic diagram of a cross section of the structure shown in FIG. 19 in one direction.
Figure 21:
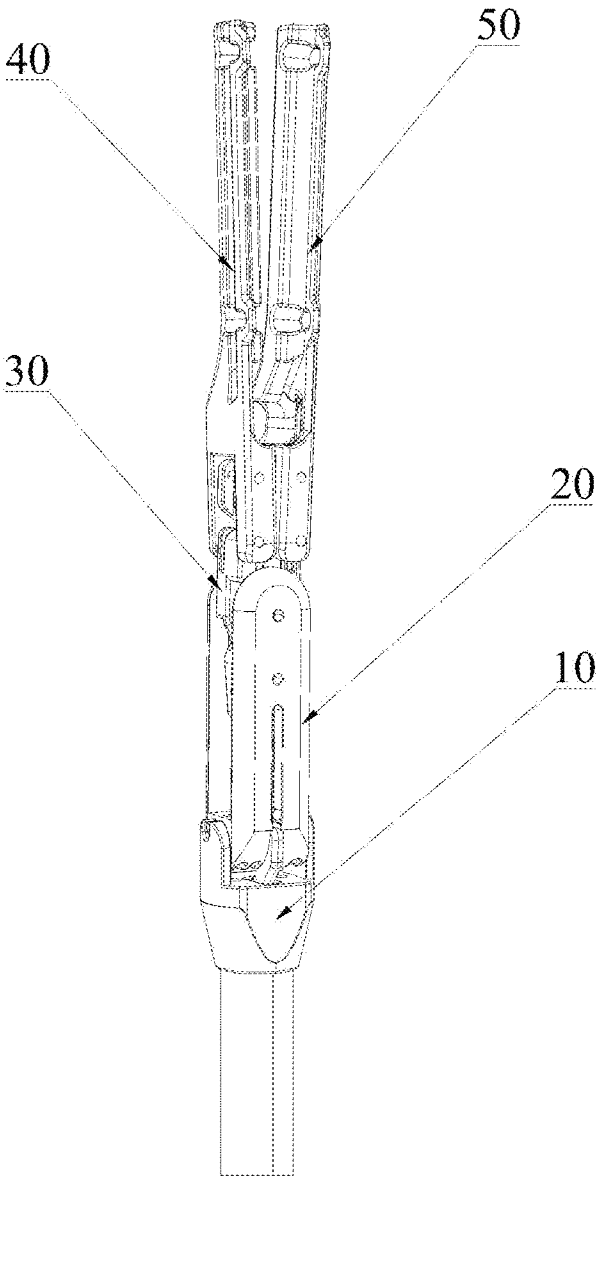
FIG. 21 is a schematic structural diagram of a delivery actuator in another embodiment of the present disclosure.
Figure 22:
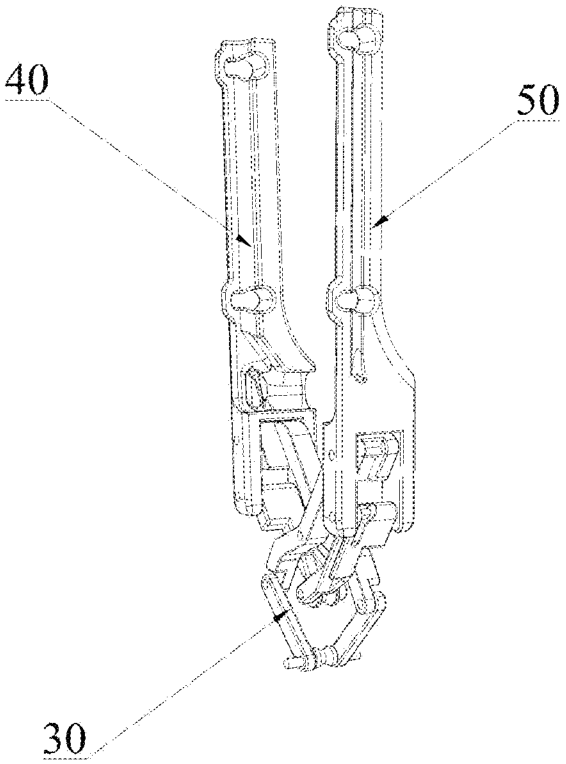
FIG. 22 is a schematic diagram of a first tong arm and a second tong arm in the embodiment shown in FIG. 21 in one view direction.
Figure 23:
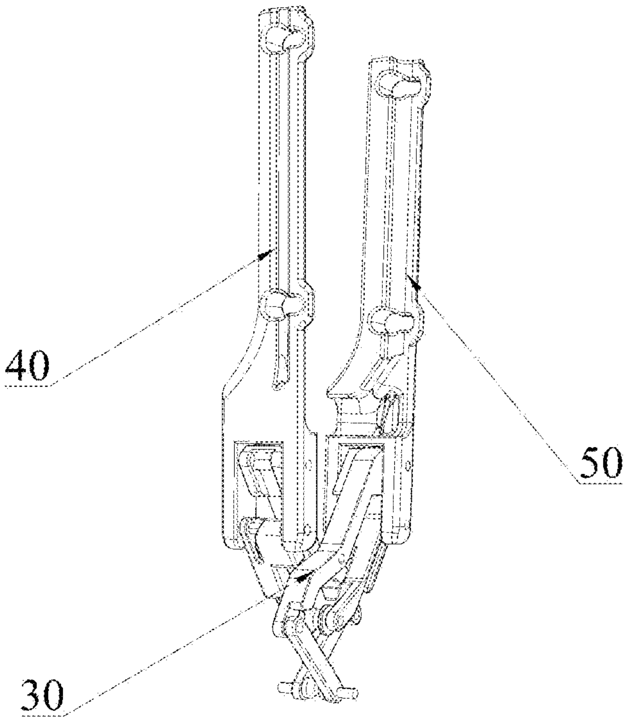
FIG. 23 is a schematic diagram of the first tong arm and the second tong arm in the embodiment shown in FIG. 21 in another view direction.
Figure 24:
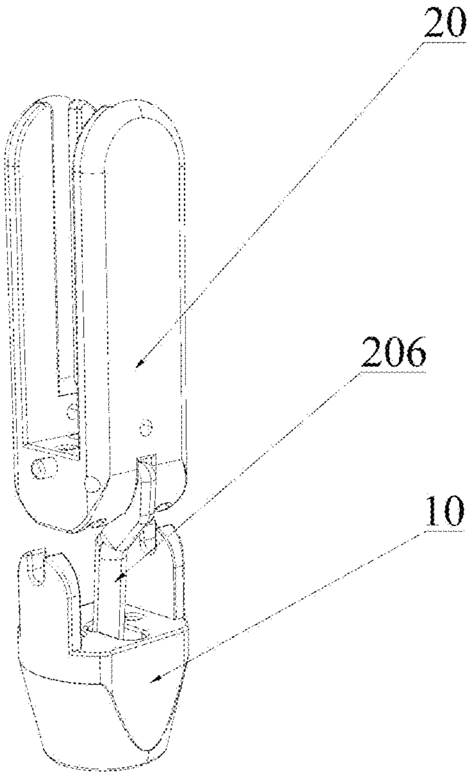
FIG. 24 is a schematic diagram of structural decomposition of a second control mechanism in the embodiment shown in FIG. 21 (a base and a swing seat are separated in a longitudinal direction of the diagram)

The second control mechanism is connected with the swing seat 20 and is configured to control the rotation of the swing seat 20 relative to the base 10. As shown in FIG. 15, the second control mechanism includes a second coiling element 70 and at least two second connecting lines L2. First ends of the at least two second connecting lines L2 are respectively connected to a first side and a second side of the swing seat 20, and the first side and the second side of the swing seat 20 are two sides of the hinged end between the swing seat 20 and the base 10 located on a rotation path (namely a left lower side and a right upper side of the swing seat 20 shown in the figures in FIG. 1 and FIG. 3). Specifically, as shown in FIG. 20, a first end of the second connecting line L2 is connected with a stop block 205, and the stop block 205 is limited and fixed to the swing seat 20 so as to fix the first end of the second connecting line L2 to the swing seat 20. The second end of the second connecting line L2 is wound on the second coiling element.

Figure 3:
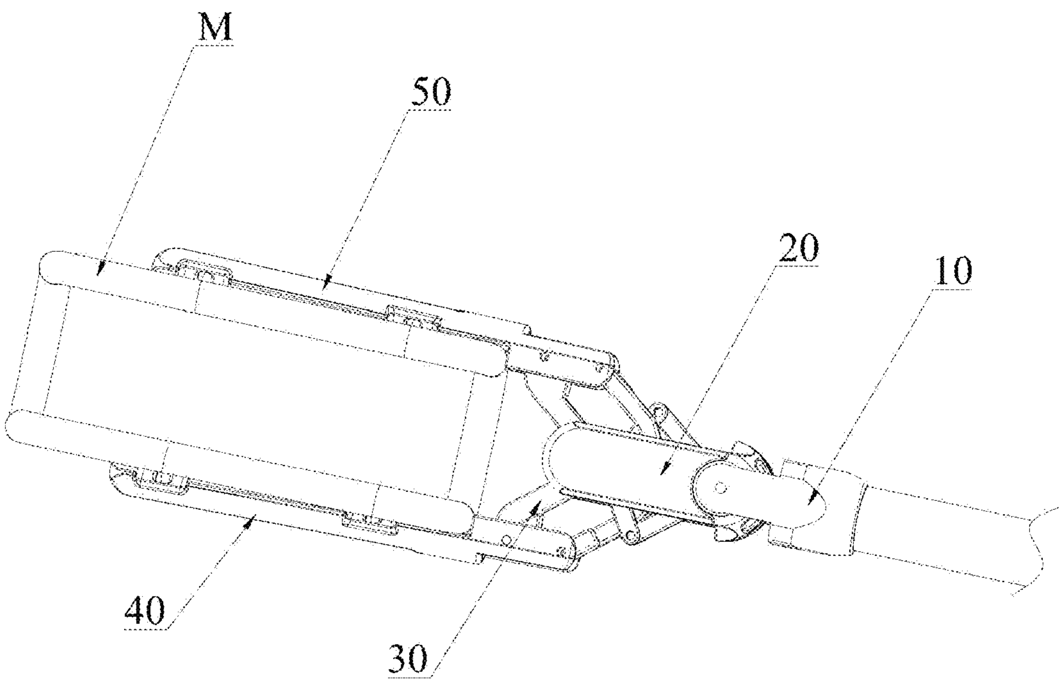
FIG. 3 is a schematic diagram of the delivery actuator shown in FIG. 1 connected with an implant and in an open state.
Figure 4:
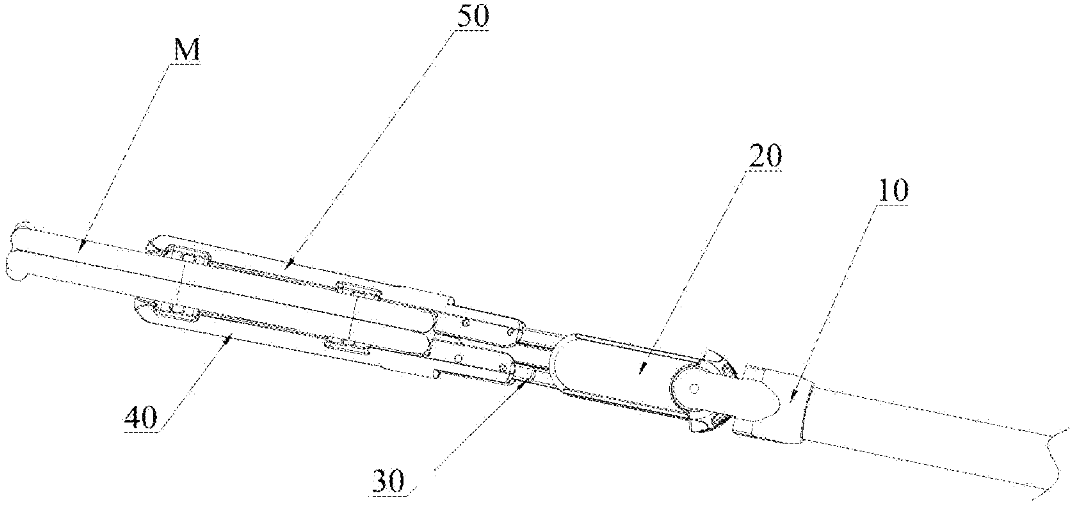
FIG. 4 is a schematic diagram of the delivery actuator shown in FIG. 1 connected with an implant and in a closed state.

With reference to FIG. 1 and FIG. 3, when the second connecting line L2 connected with the first side of the swing seat 20 applies a pulling force to the first side of the swing seat 20, the swing seat 20 can be pulled to rotate towards the direction of the first side; and when the second connecting line L2 connected with the second side of the swing seat 20 applies a pulling force to the second side of the swing seat 20, the swing seat 20 can be pulled to rotate towards the direction of the second side.

Specifically, one or a plurality of second coiling elements can be provided. When one second coiling element is provided, the second end of each second connecting line L2 can be wound on the second coiling element, but the winding directions of the second connecting lines L2 connected to the first side and second side of the swing seat 20 should be opposite. In this way, the second coiling element can rotate along different directions to respectively apply pulling forces to the second connecting lines connected to the first side and the second side of the swing seat 20, thereby controlling the swing seat 20 to rotate towards different directions.

Figure 25:
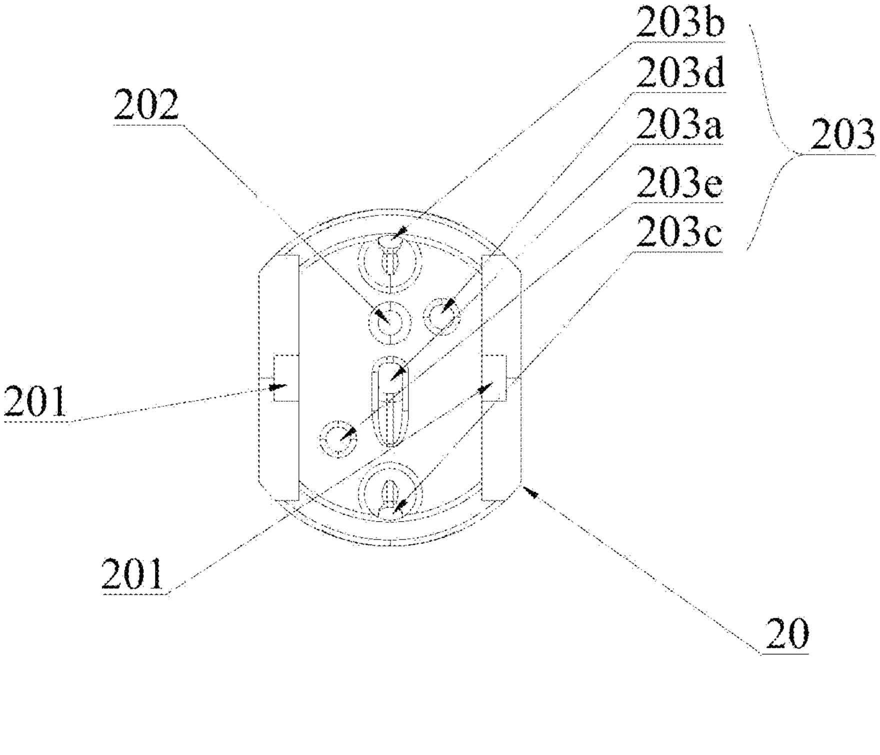
FIG. 25 is a schematic diagram of a swing seat in an embodiment in a first view direction (top view)
Figure 26:
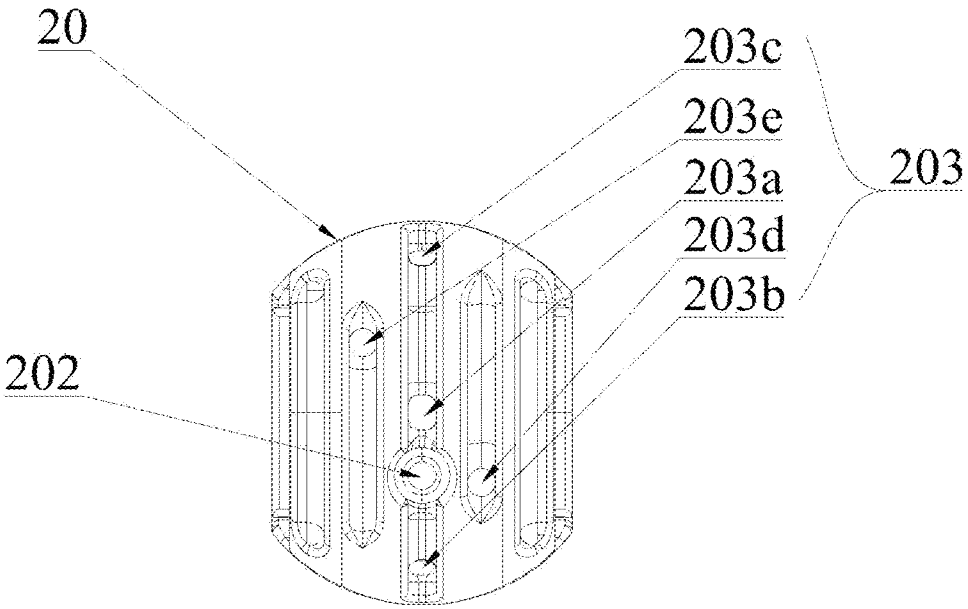
FIG. 26 is a schematic diagram of the swing seat in the embodiment in a second view direction (bottom view)

The third control mechanism is connected with the implant connected and fixed to the delivery actuator, and is configured to control the state between the implant and the first tong arm 40 and second tong arm 50 of the delivery actuator. Specifically, the third control mechanism includes a third connecting line (not shown in the figures), and the third connecting line includes a first sub-control line and a second sub-control line. The first sub-control line and the second sub-control line respectively include a binding part, a control part, and a connecting part for connecting the binding part to the control part. The swing seat 20 is provided with a fixing part. The implant is movably bound to the first tong arm 40 by the binding part of the first sub-control line, the control part of the first sub-control line is connected and fixed to the fixing part of the swing seat 20, and the control part of the first sub-control line is configured to be triggered to unbind the binding part of the first sub-control line. The implant is movably bound to the second tong arm 50 by the binding part of the second sub-control line, the control part of the second sub-control line is connected and fixed to the fixing part of the swing seat 20, and the control part of the second sub-control line is configured to be triggered to unbind the binding part of the second sub-control line. Specifically, as shown in FIG. 25 and FIG. 26, the fixing part can be the structural form of a line groove 203, and the control parts of the first sub-control line and the second sub-control line are connected and fixed to the line groove 203. For example, the fixing part for fixing the first sub-control line can be a line groove 203*d*, and the fixing part for fixing the second sub-control line can be a line groove 203*e*.

Through the binding parts of the first sub-control line and the second sub-control line, before and during the movement of the implant to the target position, the implant is bound to the first tong arm 40 and the second tong arm 50 of the delivery actuator. After the movement of the implant to the target position, taking an auricle clamp as an example, the auricle clamp moves to the left auricle to close the left auricle. In this case, the auricle clamp can be unbound from the first tong arm 40 and the second tong arm 50 outside the human body through the control parts of the first sub-control line and the second sub-control line. Therefore, after the implantation process of the implant is completed, the delivery actuator can be conveniently removed from the human body.

In an embodiment of the delivery apparatus, as shown in FIG. 21 to FIG. 24, the second control mechanism can further include a connecting rod 206, a first end of the connecting rod 206 is connected with the swing seat 20, and a joint between the connecting rod 206 and the swing seat 20 is located outside a hinge shaft between the swing seat 20 and the base 10. By this arrangement, the first end of the connecting rod 206 can act on the swing seat 20 to enable the swing seat 20 to rotate relative to the base 10. A second end of the connecting rod 206 is connected to a hand-held operating part arranged at a rear end of the delivery apparatus. When the delivery apparatus in this embodiment is used, the second end of the connecting rod 206 can be pulled, dragged, etc. on the hand-held operating part. In a case that the second end of the connecting rod 206 moves under the action of an external force, the corresponding acting force will be transmitted to the first end of the connecting rod 206 and the swing seat 20, thereby driving the swing seat 20 to rotate in a predetermined direction around the hinge shaft between the swing seat 20 and the base 10.

In this embodiment, as shown in FIG. 25 and FIG. 26, the swing seat 20 is provided with a plurality of line grooves 203, and the plurality of line grooves are used for the above first connecting line, second connecting line and third connecting line to pass through or be connected and fixed. Specifically, in this embodiment, five line grooves 203 are provided and are respectively line grooves 203*a*, 203*b*, 203*c*, 203*d*, and 203*e*, wherein the line groove 203*a* is used for the first connecting line to pass through, the line groove 203*b* and the line groove 203*c* are respectively used for the second connecting lines connected with the first side and second side of the swing seat 20 to pass through, and the line groove 203*d* and the line groove 203*e* are respectively used for the first sub-control line and second sub-control line of the third connecting line to be connected and fixed.

In this embodiment, each line groove 203 includes a generally thinner main body part 2031. The main body parts 2031 only need to be able to accommodate the first connecting line, the second connecting line, the third connecting line, etc. Moreover, under the condition of meeting this requirement, the apertures of the main body parts 2031 can be as small as possible to limit the swing amplitude of the first connecting line, the second connecting line, the third connecting line, etc. In the plurality of line grooves 203, tail ends of at least some line grooves 203 are also provided with opening parts 2032, wherein the closer the width of the opening part 2032 generally approaches the rear direction, the larger the aperture.

Figure 27:
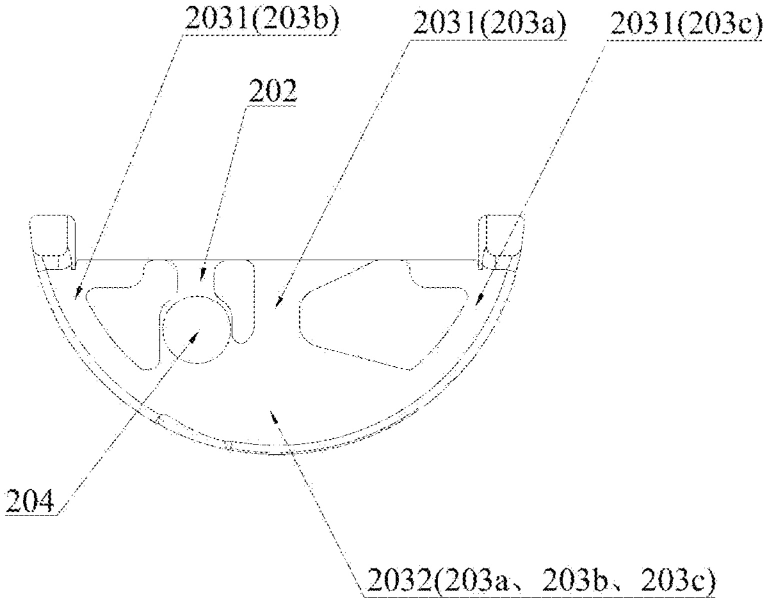
FIG. 27 is a schematic diagram of a partial structure (showing a line groove) of a cross section of the swing seat in the embodiment.
Figure 28:
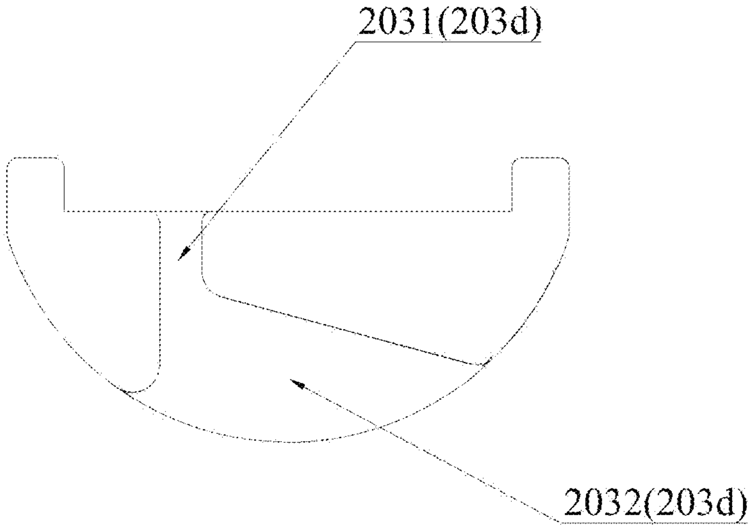
FIG. 28 is a schematic diagram of a partial structure (showing the line groove and a stop block) of another cross section of the swing seat in the embodiment.
Figure 29:
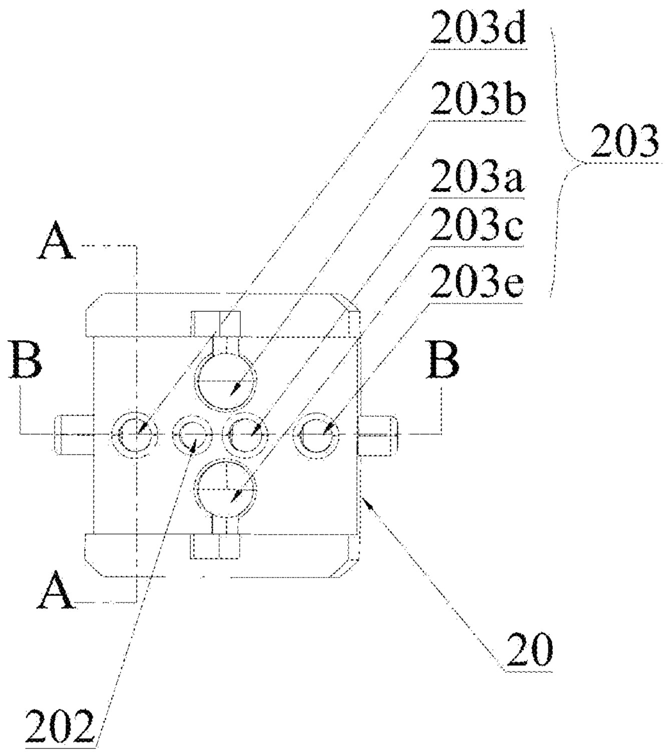
FIG. 29 is a schematic diagram of a swing seat in another embodiment in a first view direction (front-end view)
Figure 30:
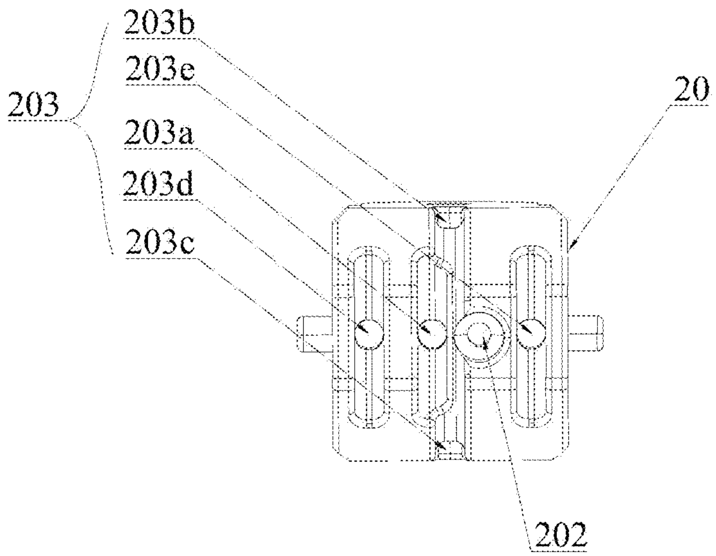
FIG. 30 is a schematic diagram of the swing seat in the another embodiment in a second view direction (rear-end view)
Figure 31:
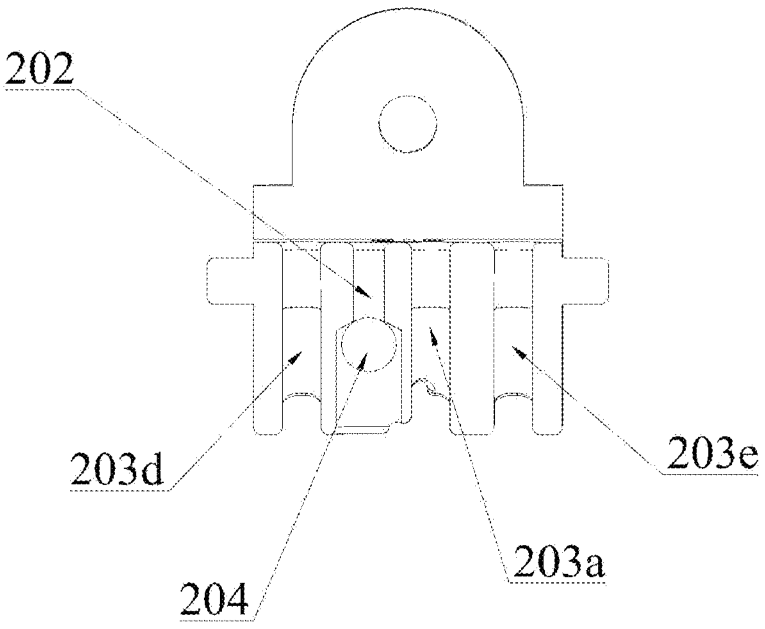
FIG. 31 is a schematic diagram of a cross-sectional structure (showing a line groove) along A-A of the swing seat in the another embodiment.

In the embodiment of the delivery apparatus based on the delivery actuator shown in FIG. 1 to FIG. 4, the line groove 203 can be as shown in FIG. 27 and FIG. 28. Taking the line groove 203*d* as an example, as shown in FIG. 28, the line groove 203*d* includes a main body part 2031 and an opening part 2032 and is configured to connect and fix the first sub-control line. When the swing seat 20 deflects to one side, the rear end of the swing seat 20 turns to the side of the base 10. In this case, the space between the swing seat 20 and the base 10 will decrease, and correspondingly, the space of the first sub-control line will be squeezed. However, in a case that the opening part 2032 is arranged along the rotational circumferential direction of the swing seat 20, the opening part 2032 can form a notch for accommodating the first sub-control line at the position of the rear end of the swing seat 20. In this way, even when the swing seat 20 rotates and the rear end of the swing seat 20 faces the side of the base 10, the first sub-control line will not be clamped between the base 10 and the swing seat 20, affecting the normal operation thereof.

In the embodiment of the delivery apparatus based on the delivery actuator shown in FIG. 1 to FIG. 4, at least two of the plurality of line grooves 203 can be arranged along the rotational circumferential direction of the swing seat 20, and the at least two line grooves 203 share the opening part 2032. As shown in FIG. 25, the line grooves 203*a*, 203*b* and 203*c* are arranged along the rotational circumferential direction of the swing seat 20 and have the common opening part 2032. In this way, the number of grooves formed at the rear end of the swing seat 20 can be reduced, so that the processing time and processing cost can be saved.

As mentioned above, as shown in FIG. 28, with reference to FIG. 25 and FIG. 26, the swing seat 20 has a first side and a second side, and the first side and the second side are two sides of the hinged end between the swing seat 20 and the base 10 located on a rotation path. The opening part 2032 of the line groove 203 located on the first side of the swing seat 20 is located on the second side of the main body part 2031 of the line groove 203; and the opening part 2032 of the line groove 203 located on the second side of the swing seat 20 is located on the first side of the main body part 2031 of the line groove 203. By this arrangement, for the line groove 203 located on the first side of the swing seat 20, partial structures of the swing seat 20 on the first side of the main body part 2031 of the line groove 203 can be retained; and for the line groove 203 located on the second side of the swing seat 20, partial structures of the swing seat 20 on the second side of the main body part 2031 of the line groove 203 can be retained. The partial structures retained on the swing seat 20 mentioned above will not interfere with the connecting line passing through the line groove 203 during the rotation of the swing seat 20. The retention of these structures can enhance the structural strength of the rear end of the swing seat 20, especially the structural strength in the direction perpendicular to the rotation plane of the swing seat 20.

Figure 32:
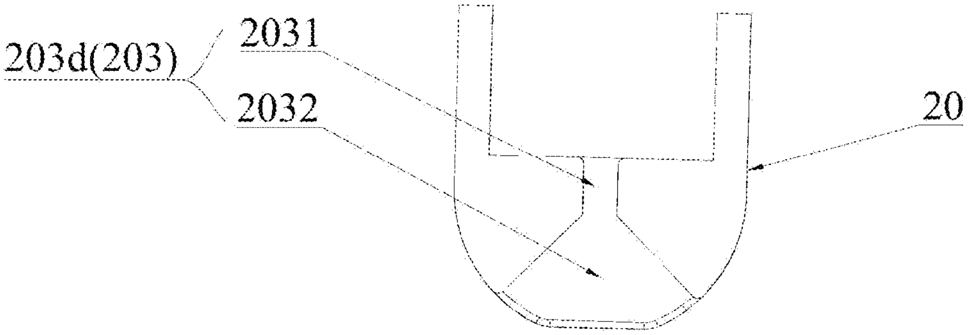
FIG. 32 is a schematic diagram of a cross-sectional structure (showing the line groove and a stop block) along B-B of the swing seat in the another embodiment.

In the embodiment of the delivery apparatus based on the delivery actuator shown in FIG. 10 to FIG. 13, the line groove 203 can be as shown in FIG. 29 to FIG. 32. Taking a line groove 203*d* as an example, as shown in FIG. 32, the line groove 203*d* includes a main body part 2031 and an opening part 2032 and is configured to connect and fix the first sub-control line. When the swing seat 20 deflects to one side, the rear end of the swing seat 20 turns to the side of the base 10. In this case, the space between the swing seat 20 and the base 10 will decrease, and correspondingly, the space of the first sub-control line will be squeezed. However, in a case that the opening part 2032 is arranged along the rotational circumferential direction of the swing seat 20, the opening part 2032 can form a notch for accommodating the first sub-control line at the position of the rear end of the swing seat 20. In this way, even when the swing seat 20 rotates and the rear end of the swing seat 20 faces the side of the base 10, the first sub-control line will not be clamped between the base 10 and the swing seat 20, affecting the normal operation thereof.

It should be noted that the relational terms herein such as "first" and "second" are used only to differentiate an entity or operation from another entity or operation, and do not require or imply any actual relationship or sequence between these entities or operations. Moreover, the terms "include", "contain" or any other variants thereof are intended to cover non-exclusive inclusions. Therefore, a process, method, article or device including a series of elements includes not only those elements, but also other elements that are not explicitly listed, or further includes elements inherent to such process, method, article or device. Without more limitations, an element defined by the statement "include one . . . " does not exclude the existence of other same elements in the process, method, article or device that includes the element.

The above descriptions are only specific implementations of the present disclosure to ensure that those skilled in the art can understand or implement the present disclosure. Various modifications to these embodiments are apparent to those skilled in the art, and the general principles defined herein may be implemented in other embodiments without departing from the spirit or scope of the present disclosure. Therefore, the present disclosure is not limited to these embodiments illustrated herein, but conforms to the broadest scope consistent with the principles and novel features disclosed in the present disclosure.

The invention claimed is:

1. A delivery apparatus, wherein the delivery apparatus comprises a controller and a delivery actuator, wherein the delivery actuator comprises a swing seat, a first tong arm, a second tong arm, and a connecting rod mechanism;

the swing seat is connected to a base and is rotatably connected to the base;

the connecting rod mechanism comprises a first connecting rod, a second connecting rod, a third connecting rod, a fourth connecting rod, a fifth connecting rod, and a sixth connecting rod;

the first connecting rod and the second connecting rod are hinged to each other, and a hinged end between the first connecting rod and the second connecting rod is located between a first end and a second end of the first connecting rod and located between a first end and a second end of the second connecting rod, so that the first connecting rod and the second connecting rod form an X-shaped scissor structure; a hinge shaft of the first connecting rod and the second connecting rod is hinged to the swing seat;

the first ends of the first connecting rod and the second connecting rod are respectively hinged to the first tong arm and the second tong arm, and the second ends of the first connecting rod and the second connecting rod are respectively hinged to first ends of the third connecting rod and the fourth connecting rod; second ends of the third connecting rod and the fourth connecting rod are hinged to each other;

first ends of the fifth connecting rod and the sixth connecting rod are respectively hinged to the first tong arm and the second tong arm, second ends of the fifth connecting rod and the sixth connecting rod are hinged to each other, and a hinge shaft of the fifth connecting rod and the sixth connecting rod is hinged to the swing seat;

the swing seat is provided with a guide groove, and the guide groove is parallel to the first tong arm and the second tong arm; and a hinge shaft of the third connecting rod and the fourth connecting rod is arranged in the guide groove and can slide along the guide groove;

wherein the controller comprises a first control mechanism, and the first control mechanism is connected with a control end of the connecting rod mechanism of the delivery actuator; and the first control mechanism comprises a first connecting line and a first coiling element, and the first connecting line is wound on the first coiling element and is connected with the control end.

2. The delivery apparatus according to claim 1, wherein a plane in which the first tong arm and the second tong arm move relative to the swing seat and a rotation plane in which the swing seat rotates relative to the base are coplanar or perpendicular to each other.

3. The delivery apparatus according to claim 1, wherein the first tong arm is provided with a first linear binding part, and an opening of the first linear binding part faces the second tong arm; and the second tong arm is provided with a second linear binding part, and an opening of the second linear binding part faces the first tong arm.

4. The delivery apparatus according to claim 3, wherein the first tong arm is provided with a first fixing groove connected with the first linear binding part, and the second tong arm is provided with a second fixing groove connected with the second linear binding part.

5. The delivery apparatus according to claim 4, wherein at least two first fixing grooves are provided, and at least two second fixing grooves are provided.

6. The delivery apparatus according to claim 3, wherein the first tong arm is provided with a first notch, and the first notch is arranged at a tail end of the first tong arm; and the second tong arm is provided with a second notch, and the second notch is arranged at a tail end of the second tong arm.

7. The delivery apparatus according to claim 1, wherein a first end of the first connecting line is connected with a stop block, the stop block abuts against a fixing hole arranged on the swing seat so as to be fixed, and the first connecting line passes through the fixing hole and is wound around the control end, so that the first connecting line forms a pulley structure at the control end.

8. The delivery apparatus according to claim 1, wherein the delivery apparatus further comprises a second control mechanism, and the second control mechanism is connected with the swing seat and is configured to control a rotation of the swing seat relative to the base.

9. The delivery apparatus according to claim 8, wherein the second control mechanism comprises a second coiling element and at least two second connecting lines, first ends of the at least two second connecting lines are respectively connected to a first side and a second side of the swing seat, and the first side and the second side of the swing seat are two sides of a hinged end between the swing seat and the base located on a rotation path; second ends of the at least two second connecting lines are all wound on the second coiling element; or the second control mechanism comprises a connecting rod, a first end of the connecting rod is connected with the swing seat, a joint between the connecting rod and the swing seat is located outside a hinge shaft between the swing seat and the base, and a second end of the connecting rod is connected to a hand-held operating part arranged at a rear end of the delivery apparatus.

10. The delivery apparatus according to claim 1, wherein the swing seat is provided with a plurality of line grooves, and tail ends of at least some of the line grooves are provided with opening parts.

11. The delivery apparatus according to claim 10, wherein a first end of the first connecting line is connected with a stop block, the stop block abuts against a fixing hole arranged on the swing seat so as to be fixed, and the first connecting line passes through the fixing hole and is wound around the control end, so that the first connecting line forms a pulley structure at the control end.

12. The delivery apparatus according to claim 8, wherein the swing seat is provided with a plurality of line grooves, and tail ends of at least some of the line grooves are provided with opening parts.

* * * * *